US010234462B2

(12) United States Patent
Block et al.

(10) Patent No.: US 10,234,462 B2
(45) Date of Patent: Mar. 19, 2019

(54) USE OF MIMECAN IN THE ASSESSMENT OF HEART FAILURE

(75) Inventors: Dirk Block, Bichl (DE); Sara Arab, Toronto (CA); Georg Hess, Mainz (DE); Hendrik Huedig, Penzberg (DE); Peter Liu, Toronto (CA); Ursula-Henrike Wienhues-Thelen, Krailing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/359,276

(22) Filed: Jan. 26, 2012

(65) Prior Publication Data
US 2012/0156703 A1 Jun. 21, 2012

Related U.S. Application Data

(63) Continuation of application No. PCT/EP2010/004521, filed on Jul. 23, 2010.

(30) Foreign Application Priority Data

Jul. 27, 2009 (EP) .................... 09009666

(51) Int. Cl.
G01N 33/68 (2006.01)
(52) U.S. Cl.
CPC ..... *G01N 33/6893* (2013.01); *G01N 33/6812* (2013.01); *G01N 2333/4703* (2013.01); *G01N 2800/325* (2013.01)
(58) Field of Classification Search
CPC ........... G01N 33/6893; G01N 33/6812; G01N 2333/4703; G01N 2800/325
(Continued)

(56) References Cited

U.S. PATENT DOCUMENTS

| 5,807,522 A | 9/1998 | Brown |
| 6,174,686 B1 | 1/2001 | Buechler |

(Continued)

FOREIGN PATENT DOCUMENTS

| DE | 102007010834 | 11/2009 |
| EP | 0394819 | 10/1990 |

(Continued)

OTHER PUBLICATIONS

Petretto et al., 2008. Integrated genomic approaches implicate osteoglycin (Ogn) in the regulation of left ventricular mass. Nature Genetics 40: 546-552 and Supplementary Items.*

(Continued)

*Primary Examiner* — Gailene Gabel
(74) *Attorney, Agent, or Firm* — Stinson Leonard Street LLP

(57) ABSTRACT

The disclosure relates to assessing heart failure in vitro by measuring the concentration of the marker mimecan in a sample, and optionally measuring in the sample the concentration of one or more other marker(s) of heart failure, and of assessing heart failure by comparing the concentration of mimecan and the one or more other marker(s) to reference concentrations of this (or these) marker(s) as established in a reference population. The one or more markers may be selected from the group comprising a natriuretic peptide marker, a cardiac troponin marker, and a marker of inflammation. Also disclosed are the use of mimecan as a marker protein in the assessment of heart failure, a marker combination comprising mimecan, and a kit for measuring mimecan.

14 Claims, 5 Drawing Sheets

Specification includes a Sequence Listing.

(58) Field of Classification Search
USPC ...... 435/7.1, 7.8, 7.92, 7.94, 7.95, 973, 975; 436/501, 503, 518, 86, 811; 530/388.2, 530/388.23, 388.24, 388.9, 389.2, 389.8, 530/395
See application file for complete search history.

(56) References Cited

U.S. PATENT DOCUMENTS

| | | | |
|---|---|---|---|
| 6,333,397 B1 | 12/2001 | Katus | |
| 6,376,206 B1 | 4/2002 | Katus | |
| RE39,816 E * | 9/2007 | Stanton et al. | 435/7.92 |
| 7,713,705 B2 * | 5/2010 | Buechler | C12Q 1/6883 422/68.1 |
| 7,732,214 B2 * | 6/2010 | Hess et al. | 436/86 |
| 2002/0068319 A1 * | 6/2002 | Ni et al. | 435/69.1 |
| 2004/0121343 A1 * | 6/2004 | Buechler | C12Q 1/6883 435/6.14 |
| 2007/0218498 A1 * | 9/2007 | Buechler et al. | 435/7.1 |

FOREIGN PATENT DOCUMENTS

| | | |
|---|---|---|
| EP | 1967853 | 9/2008 |
| EP | 1995596 | 11/2008 |
| WO | WO 2000/045176 | 8/2000 |
| WO | 02/23191 * | 3/2002 |
| WO | WO 2004/099253 | 11/2004 |
| WO | WO 2004/105784 | 12/2004 |
| WO | 2006/026557 A3 | 3/2006 |
| WO | WO 2006/043031 | 4/2006 |
| WO | WO 2006/099336 | 9/2006 |
| WO | WO 2008/089994 | 7/2008 |
| WO | 2009/047285 A1 | 4/2009 |
| WO | WO 2009/061382 | 5/2009 |

OTHER PUBLICATIONS

Cook et al., 1999. Regulation of Bcl-2 family proteins during development and in response to oxidative stress in cardiac myocytes. Circ. Res. 85: 940-949.*
Sabatine et al., 2002. Multimarker approach to risk statification in non-ST elevation acute coronary syndromes: simultaneous assessment of Troponin-I, C-reactive protein, and B-type natriuretic peptide. Circulation 105: 1760-1763.*
International Search Report dated Sep. 15, 2010 in PCT Application No. PCT/EP2010/004521, 5 pages.
"ACC/AHA 2005 Guideline Update for the Diagnosis and Management of Chronic Heart Failure in the Adult" (S. Hunt et al., www.acc.org, the ACC/AHA practice guidelines), (2005).
AHA Statistical Update, Heart Disease and Stroke Statistics—2008 Update, Dallas, Texas, American Heart Association (2008).
Ameye, L. and Young, M.F., Mice deficient in small leucine-rich proteoglycans: novel in vivo models for osteoporosis, osteoarthritis, Ehlers-Danlos syndrome, muscular dystrophy, and corneal diseases, Glycobiology 12 (2002) 107R-116R.
Asahi, M., et al., "Cardiac-specific overexpression of sarcolipin inhibits sarco(endo)plasmic reticulum $Ca^{2+}$ATPase (SERCA2a) activity and impairs cardiac function in mice," Proc. Natl. Acad. Sci. USA 101 (2004) 9199-9204.
Barth, A.S. et al., "Identification of a Common Gene Expression Signature in Dilated Cardiomyopathy Across Independent Microarray Studies," J. American College of Cardiology 48 (2006) 1610-1617.
Beck-Da-Silva, L., et al., BNP-Guided Therapy Not Better Than Expert's Clinical Assessment for β-Blocker Titration in Patients With Heart Failure, Congest. Heart Fail. 11 (2005) 248-253, quiz 254-255.
Benamer, H., et al., "Comparison of the Prognostic Value of C-Reactive Protein and Troponin I in Patients With Unstable Angina Pectoris," Am. J. Cardiol. 82 (1998) 845-850.

Benjamini, Y., and Hochberg, Y., "Controlling the False Discovery Rate: a Practical and Powerful Approach to Multiple Testing," Journal of the Royal Statistical Society B. 57 (1995) 289-300.
Breiman, L., "Random Forests," Machine Learning 45 (2001) 5-32.
Burmeister, G., and Gallacchi, G., A Selective Method for Determining MRP8 and MRP14 Homocomplexes and Heterocomplexes by Sandwich ELISA for the Discrimination of Active and Non-Active Osteoarthritis from Rheumatoid Arthritis . . . Inflammopharmacology 3 (1995) 221-230.
Christenson, R.H., et al., "Cardiac troponin T and cardiac troponin I: relative values in short-term risk stratification of patients with acute coronary syndromes," Clin. Chem. 44 (1998) 494-501.
Cleveland, W.S. and Devlin, S.J., "Locally Weighted Regression: An Approach to Regression Analysis by Local Fitting," Journal of the American Statistical Association 83 (1988) 596-610.
De Tombe, P.P., "Altered contractile function in heart failure," Cardiovasc. Res. 37 (1998) 367-380.
Fernandez, B. et al., "Osteoglycin expression and localization in rabbit tissues and atherosclerotic plaques," Mol. Cell. Biochem. 246 (2003) 3-11.
Foell, D., et al., Expression of the pro-inflammatory protein S100A12 (EN-RAGE) in rheumatoid and psoriatic arthritis, Rheumathology 42 (2003) 1383-1389.
Friedman, J.H., "Regularized Discriminant Analysis," J. of the American Statistical Association 84 (1989) 165-175.
Gearing, A.J. and Hemingway, I., "Soluble Forms of Vascular Adhesion Molecules, E-Selectin, ICAM-1, and VCAM-1: Pathological Significance," Ann. N.Y. Acad. Sci. 667 (1992) 324-331.
Gremmler, B., et al., "Relation between N-terminal pro-brain natriuretic peptide values and invasively measured left ventricular hemodynamic indices," Exp. Clin. Cardiol. 8 (2003) 91-94.
Gustafsson, F., et al., "Diagnostic and Prognostic Performance of N-Terminal ProBNP in Primary Care Patients With Suspected Heart Failure," J. Card. Fail. 11, Suppl. 5 (2005) S15-20.
Hamajima, S. et al., "Effect of low-level laser irradiation on osteoglycin gene expression in osteoblasts," Lasers Med. Sci. 18 (2003) 78-82.
Hamm, C.W., et al., "The Prognostic Value of Serum Troponin T in Unstable Angina," N. Engl. J. Med. 327 (1992) 146-150.
Hunt, P.J., et al., "The Amino-Terminal Portion of Pro-Brain Natriuretic Peptide (Pro-BNP) Circulates in Human Plasma," Biochem. Biophys. Res. Com. 214 (1995) 1175-1183.
Hunt, P.J., et al.,"The Role of the Circulation in Processing pro-Brain Natriuretic Peptide (proBNP) to Amino-Terminal BNP and BNP-32," Peptides 18 (1997) 1475-1481.
Katus, H.A., et al., "Enzyme Linked Immuno Assay of Cardiac Troponin T for the Detection of Acute Myocardial Infarction in Patients," J. Mol. Cell. Cardiol. 21 (1989) 1349-1353.
Kislinger, T., et al., "PRISM, a Generic Large Scale Proteomic Investigation Strategy for Mammals," Mol. Cell Proteom. 2 (2003) 96-106.
McDonagh, T.A., et al., "NT-proBNP and the diagnosis of heart failure: a pooled analysis of three European epidemiological studies," Eur. J. Heart Fail. 6 (2004) 269-273.
Molkentin, J.D., "Cytoplasmic Signaling Pathways That Regulate Cardiac Hypertrophy," Ann. Rev. Physiol. 63 (2001) 391-426.
Mueller, T., et al., "Long-term stability of endogenous B-type natriuretic peptide (BNP) and amino terminal proBNP (NT-proBNP) in frozen plasma samples," Clin. Chem. Lab. Med. 42 (2004) 942-944.
Ohman, E.M., et al., "Cardiac Troponin T Levels for Risk Stratification in Acute Myocardial Ischemia," N. Engl. J. Med. 335 (1996) 1333-1341.
Oudit, G.Y., et al., "L-type $Ca^{2+}$channels provide a major pathway for iron entry into cardiomyocytes in iron-overload cardiomyopathy," Nat. Med. 9 (2003) 1187-1194.
Petretto, E. et al., "Integrated genomic approaches implicate osteoglycin (Ogn) in the regulation of left ventricular mass," Nature Genetics 40 (2008) 546-552.
Piano, M.R., et al., "Cellular Events Linked to Cardiac Remodeling in Heart Failure: Targets for Pharmacologic Intervention," J. Cardiovasc. Nurs. 14 (2000) 1-23.

(56) References Cited

OTHER PUBLICATIONS

Robinson, W.H., et al., "Proteomics Technologies for the Study of Autoimmune Disease," Arthritis Rheum. 46 (2002) 885-893.
Robinson, W.H., et al., "Autoantigen microarrays for multiplex characterization of autoantibody responses," Nat. Med. 8 (2002) 295-301.
Ruczinski, I., et al., "Logic Regression," J. of Computational and Graphical Statistics 12 (2003) 475-511.
Schmitt, J.P., et al., "Dilated Cardiomyopathy and Heart Failure Caused by a Mutation in Phospholamban," Science 299 (2003) 1410-1413.
Shanahan, C.M. et al., "Identification of Osteoglycin as a Component of the Vascular Matrix, Differential Expression by Vascular Smooth Muscle Cells During Neointima Formation and in Atherosclerotic Plaques," Arter. Thromb. Vasc. Biol. 17 (1997) 2437-2447.
Smith, M.W., et al., "Delayed metabolism of human brain natriuretic peptide reflects resistance to neutral endopeptidase," J. Endocrinol. 167 (2000) 239-246.
Tasheva, E.S. et al., "Mimecan/osteoglycin-deficient mice have collagen fibril abnormalities," Mol. Vis. 8 (2002) 407-415.
Triepels R.H., et al., "N-terminal pro-brain natriuretic peptide (NT-proBNP) as screening test for early stage heart failure," Clin. Chem. 49, Suppl. A (2003) A37-A38.
Wang, Y. et al., "Differential Expression of Mimecan and Thioredoxin Domain-Containing Protein 5 in Colorectal Adenoma and Cancer: A Proteomic Study," Exp. Biol. Med. 232 (2007) 1152-1159.
Wu, A.H., et al., "Analytical and Clinical Evaluation of the Bayer ADVIA Centaur Automated B-Type Natriuretic Peptide Assay in Patients with Heart Failure: A Multisite Study," Clin. Chem. 50 (2004) 867-873.
Zweig, M.H., and Campbell, G., "Receiver-Operating Characteristic (ROC) Plots: A Fundamental Evaluation Tool in Clinical Medicine," Clin. Chem. 39 (1993) 561-577.
Dasch, J. R. et al., "Characterization of Momoclonal Antibodies Recognizing Bovine Bone Osteoglycin," Connective Tissue Research 30 (1993) 11-21.
De Simone, G. et al.,"Left ventricular mass predicts heart failure not related to previous myocardial infarction: the Cardiovascular Health Study," European Heart Journal 29 (2008) 741-747.
Markus, M.R.P. et al., "Left Ventricular Mass in Patients with Heart Failure," Arquivos Brasileiros de Cardiologia 83 (2004) 232-236.
Hu, S.-M. et al., "The Mimecan Gene Expressed in Human Pituitary and Regulated by Pituitary Transcription Factor-1 as a Marker for Diagnosing Pituitary Tumors," Journal of Clinicial Endocrinology & Metabolism, vol. 90, No. 12, Dec. 1, 2005, pp. 6657-6664.
"Abnormal behavior of osteoglycin gene linked to heart and kidney problems," The Medical News [Online] Apr. 28, 2008, Retrieved from the internet Feb. 10, 2012, http://www.news-medical.net/news/2008/04/28/37830.aspx.
"Gene sind fuer Vergroesserung des Herzens mitverantwortlich" Nedine [Online] Jun. 9, 2008, Retrieved from the Internet Nov. 24, 2009, http://www.nedine.org/newsitem.mc?id=14027, with English translation.

* cited by examiner

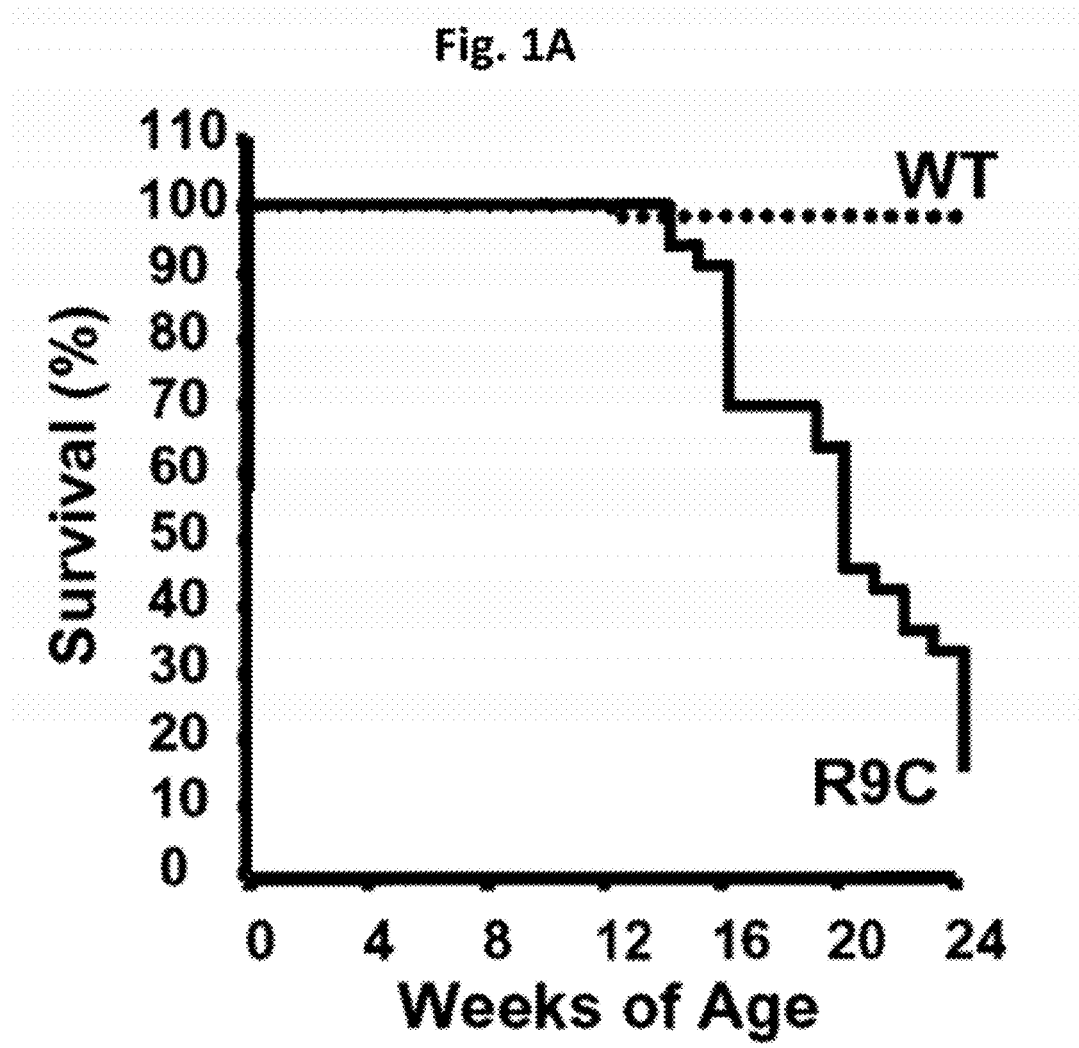

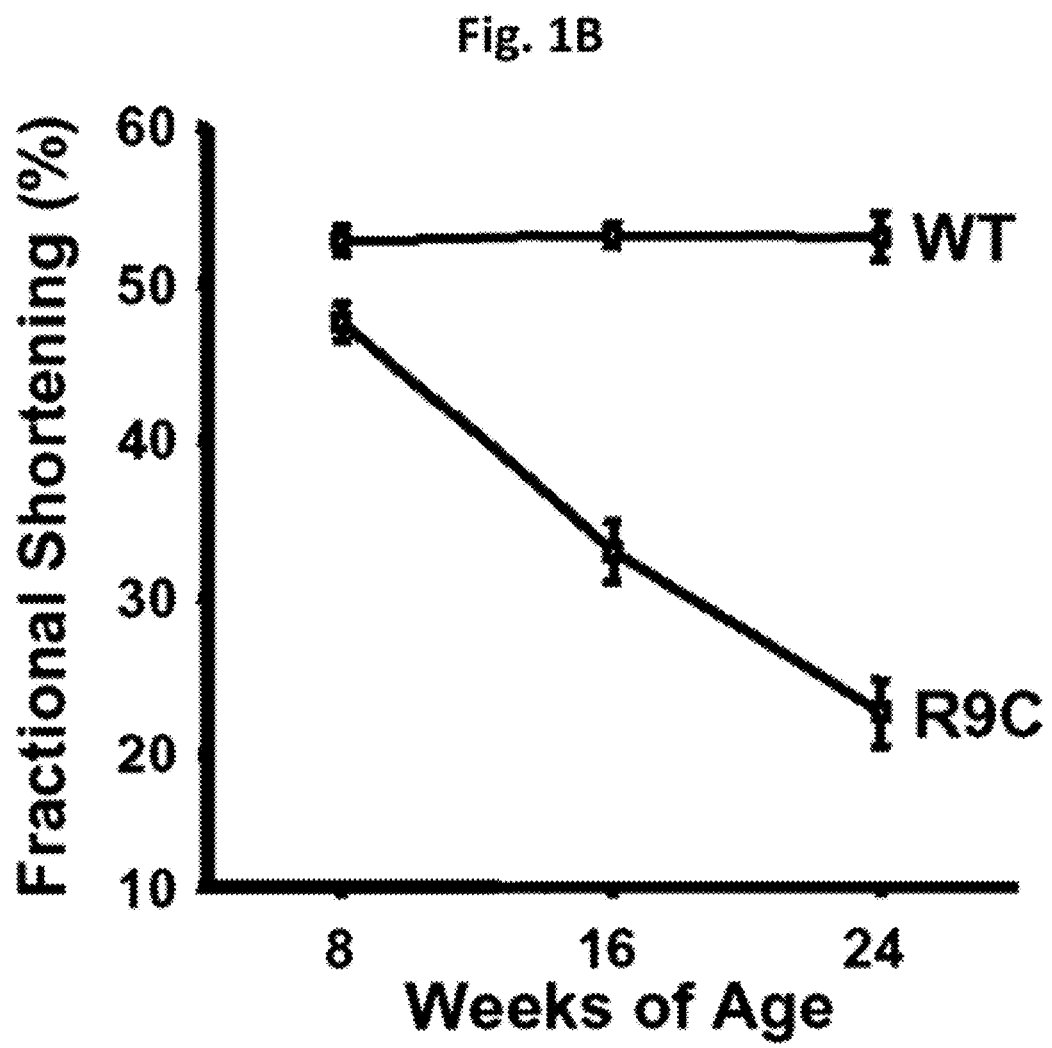

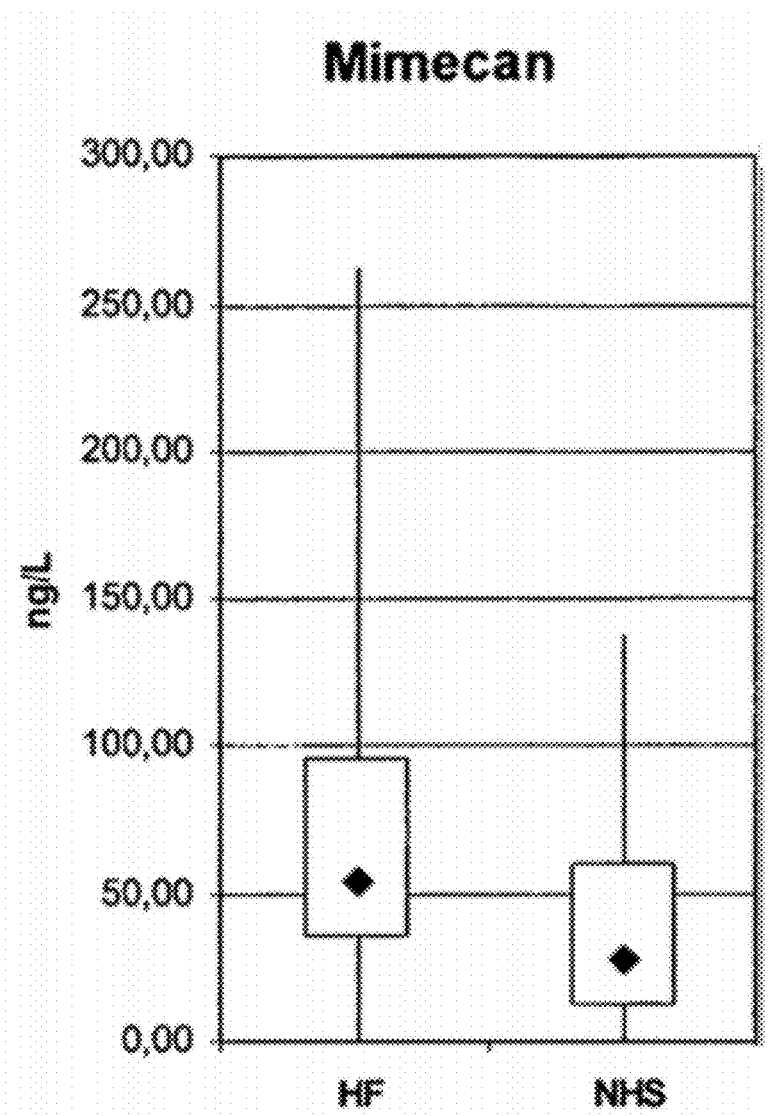

USE OF MIMECAN IN THE ASSESSMENT OF HEART FAILURE

RELATED APPLICATIONS

This application is a continuation of International Application No. PCT/EP2010/004521, filed Jul. 23, 2010, which claims the benefit of European Patent Application No. 09009666.0, filed Jul. 27, 2009, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 26, 2012, is named SEQUENCE_LISTING_26218US.txt, and is 2,823 bytes in size.

FIELD OF THE DISCLOSURE

The present disclosure relates to the assessment and diagnosis of heart failure ("HF"). More specifically, the present disclosure relates to a marker, or combination of markers, and methods for assessing (and, in some cases, diagnosing) HF in an individual. The present disclosure also relates to kits, comprising one or more biochemical markers, for assessing (and, in some cases, diagnosing) HF.

BACKGROUND OF THE DISCLOSURE

Heart failure ("HF") is a major and growing public health problem. In the United States, for example, approximately 5 million patients have HF and over 550,000 patients are diagnosed with HF for the first time each year. (American Heart Association, Heart Disease and Stroke Statistics: 2008 Update, Dallas, Tex., American Heart Association (2008)). Similarly, statistics show that in the U.S. HF is the primary reason for 12 to 15 million office visits and 6.5 million hospitalization days each year. From 1990 to 1999, the annual number of hospitalizations has increased from approximately 810,000 to over 1 million in which HF is the primary diagnosis, and from 2.4 to 3.6 million in which HF is a primary or secondary diagnosis. In 2001, nearly 53,000 patients died of HF as a primary cause. HF is primarily a condition of the elderly, and thus the widely recognized "aging of the population" also contributes to the increasing incidence of HF. The incidence of HF is approaching 10 per 1000 in the population after age 65. In the US alone, the total estimated direct and indirect costs for HF in 2005 were approximately $27.9 billion and approximately $2.9 billion annually is spent on drugs for the treatment of HF. (Id.).

Heart Failure is characterized by a loss in the heart's ability to pump as much blood as the body needs. Failure does not mean that the heart has stopped pumping but that it is failing to pump blood as effectively as it should.

The New York Heart Association ("NYHA") and the American Association of Cardiology/American Heart Association ("ACC/AHA") have both established functional classes of HF to gauge the progression of the disease. The NYHA classification scheme has four classes of disease state: Class 1 is asymptomatic at any level of exertion; Class 2 is symptomatic at heavy exertion; and Classes III and IV are symptomatic at light and no exertion, respectively. The ACC/AHA also has a four stage scheme: Stage A is asymptomatic but is at risk for developing HF; Stage B has evidence of cardiac dysfunction without symptoms; Stage C has evidence of cardiac dysfunction with symptoms; and Stage D has symptoms of HF despite maximal therapy.

HF is appreciated in the medical community as a complex disease. It may be caused by the occurrence of a triggering event such as a myocardial infarction (heart attack) or be secondary to other causes such as hypertension, diabetes or cardiac malformations such as valvular disease. Myocardial infarction or other causes of HF result in an initial decline in the pumping capacity of the heart, for example by damaging the heart muscle. This decline in pumping capacity may not be immediately noticeable due to the activation of one or more compensatory mechanisms. However, the progression of HF has been found to be independent of the patient's hemodynamic status. Therefore, the damaging changes caused by the disease are present and ongoing even while the patient remains asymptomatic. In fact, the compensatory mechanisms which maintain normal cardiovascular function during the early phases of HF may actually contribute to progression of the disease in the long run, such as by exerting deleterious effects on the heart and its capacity to maintain a sufficient level of blood flow in the circulation, for example.

Presently, the most (or at least one of the most) useful diagnostic tests in the evaluation of patients with HF is the comprehensive 2-dimensional echocardiogram coupled with Doppler flow studies to determine whether abnormalities of myocardium, heart valves, or pericardium are present and which chambers of the heart are involved. These tests aim to answer three fundamental questions: 1) is the left ventricular ejection fraction ("LVEF") preserved or reduced, 2) is the structure of the left ventricle ("LV") normal or abnormal, and 3) are there other structural abnormalities such as valvular, pericardial, or right ventricular abnormalities which may account for the clinical presentation(s). Answers to these questions may be quantified with a numerical estimate of ejection fraction ("EF"), measurement of ventricular dimensions and/or volumes, measurement of wall thickness, and/or evaluation of chamber geometry and regional wall motion. Right ventricular size and systolic performance may be assessed, atrial size may be determined semi quantitatively, and left atrial dimensions and/or volumes may also be measured.

Noninvasive hemodynamic data acquired at the time of echocardiography may also be correlated with other diagnostic information (described above) for patients with preserved or reduced EF. Combined quantification of the mitral valve inflow pattern, pulmonary venous inflow pattern, and mitral annular velocity provides data about characteristics of LV filling and left atrial pressure. Evaluation of the tricuspid valve regurgitant gradient coupled with measurement of inferior vena caval dimension and its response during respiration provides an estimate of systolic pulmonary artery pressure and central venous pressure.

Stroke volume may also be determined with combined dimension measurement and pulsed Doppler in the LV outflow tract. However, abnormalities can be present in any of these parameters in the absence of HF. No one of these necessarily correlates specifically with HF; however, a totally normal filling pattern argues against clinical HF.

From a clinical perspective, the disease is clinically asymptomatic in the compensatory and early decompensatory phases, e.g., completely asymptomatic in stage A and having structural heart disease but no signs and symptoms of HF in stage B (as explained in the above described ACC/AHA practice guidelines). Outward signs of the disease (such as shortness of breath) do not appear until well into the decompensatory phase (i.e., stages C and D according to the ACC/AHA guidelines). Current diagnosis is based on the outward symptoms of patients in stages C and D.

Because individuals at risk of developing HF are generally free of clinical HF symptoms until the later decompensatory stages of HF, the current diagnostic tests are not ideal for early assessment of patients at risk of HF. Further, there are no known, established biochemical markers for the reliable pre-symptomatic assessment of HF. In general, by the time a HF diagnosis is established, HF is already well underway.

At least in-part due to late diagnosis, 50% of patients with HF die within two years of diagnosis. The 5-year survival rate is less than 30%. Furthermore, patients with heart failure typically receive a standard treatment including drugs which interact with specific mechanisms involved in heart failure. There are no diagnostic tests that reflect those specific mechanisms reliably and help the physician to choose the right drug (and dose) for the right patient (e.g., ACE inhibitor, AT II, β-blockers, etc).

As indicated by the above, there exists a need for an improvement in the early assessment and diagnosis of individuals at risk for HF. Thus a marker useful in assessing individuals at risk for HF which, on its own or in combination with other diagnostics evaluations, has a high positive predictive value for HF is of high clinical and practical value. Additionally, a marker (or combination of markers) for aiding in the assessment of a patient with HF is also of value for further technical progress in this clinically important area.

SUMMARY OF THE DISCLOSURE

The present disclosure provides a marker, mimecan, (or combination of markers including mimecan), and methods of utilizing the mimecan marker for the assessment (and in some cases diagnosis) of heart failure ("HF").

As disclosed herein, a mimecan marker can aid in the assessment of HF. In one embodiment of the present disclosure, a mimecan marker (and combination in some cases) as disclosed herein can help to assess whether an individual is at risk of developing heart failure. In a further aspect the marker(s) disclosed herein can aid in the assessment of disease progression. In another embodiment, such can aid in predicting the onset of HF. In another embodiment, mimecan (alone or in combination) can aid in assessing and selecting an appropriate treatment regimen to prevent or treat HF.

According to an embodiment of a method disclosed herein, the method includes the steps of measuring, in a sample obtained from an individual, the concentration of a mimecan marker and optionally measuring the concentration of one or more other marker(s) in the sample. The method also includes the step of comparing the concentration of the mimecan marker, and optionally the concentration(s) of the one or more markers from the sample, to a concentration of the marker(s) as established in a control sample.

According to another embodiment of the instant disclosure, the use of mimecan as a marker protein in the assessment of heart failure is disclosed. Additionally, a marker combination comprising mimecan is also disclosed herein. Further, a kit for measuring mimecan is disclosed herein.

Another embodiment of the instant disclosure provides a kit for performing a method for assessing HF in vitro. According to an embodiment, the kits enables performing a method comprising the steps of measuring in a sample the concentration of a mimecan marker and optionally measuring in the sample the concentration of one or more other marker(s) for HF. The kits further provides for assessing HF by comparing the concentration of the mimecan marker, and optionally the concentration(s) of the one or more other markers, to each other and/or an established control concentration of this (or these) marker(s) as established in a reference population. According to some embodiments of the present disclosure, the kit comprises reagents required to specifically measure mimecan and the optionally one or more other markers of HF.

Additional aspects and advantages of the present disclosure will be apparent in view of the description which follows. It should be understood, however, that the detailed description and the specific examples, while providing exemplified embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawings.

FIG. 1A is a phenotypic analysis of wild type (n=79) and R9C (n=44) mice presenting a survival curves for the mice generated following a 24 week period;

FIG. 1B is a phenotypic analysis of the mice from FIG. 1A, presenting cardiac shortening ("fractional shortening") assessed by echocardiography and showing significant functional impairment in the R9C transgenic animals beginning as early as 8 weeks of age;

FIG. 3 presents mimecan values measured from samples derived from 241 patients with HF (labelled "HF") and healthy human controls (labelled "NHS" for normal human serum) (the box-and-whisker-plots show the lower and upper quartiles (boxes) as well as the highest and lowest values (whiskers)).

Figure 2A:
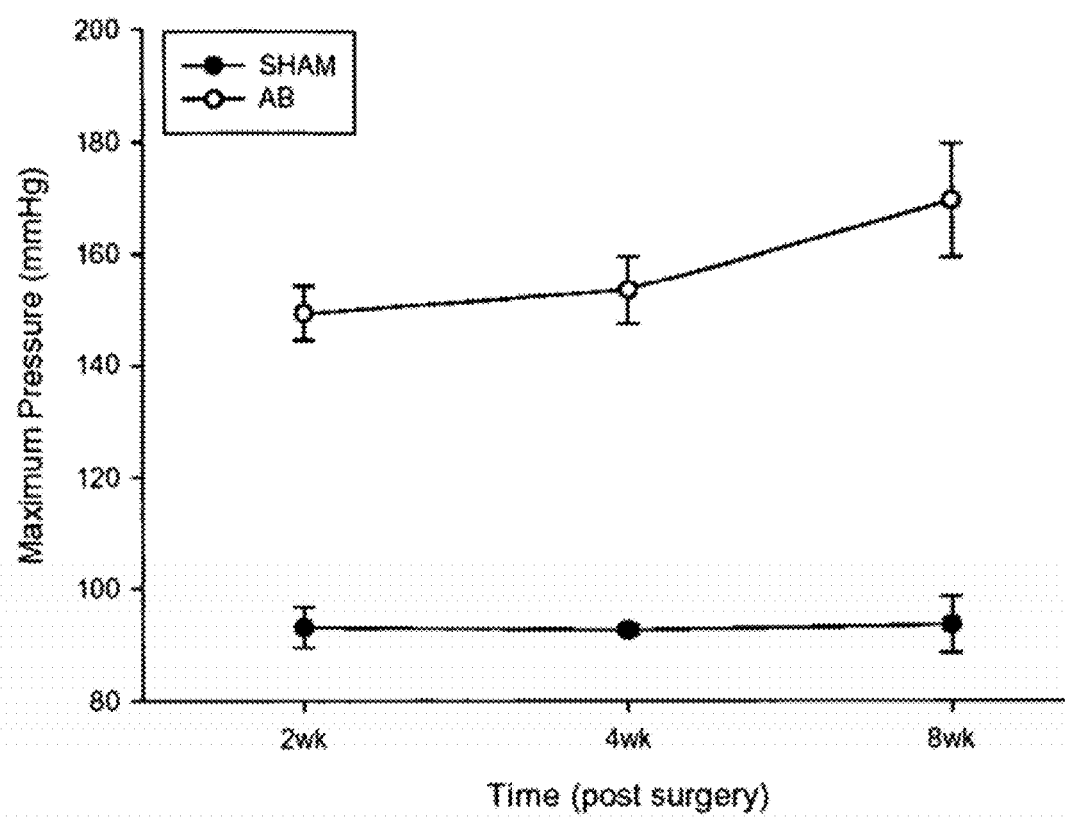
FIG. 2A is a graph depicting the changes in maximum pressure (in mmHg) at 2, 4, and 8 weeks post-surgery, as determined by echocardiograph and hemodynamic parameters, from wild type and AB mice (closed circles indicate the data from sham operated mice and open circles indicate the data from mice with aortic binding (AB))
Figure 2B:
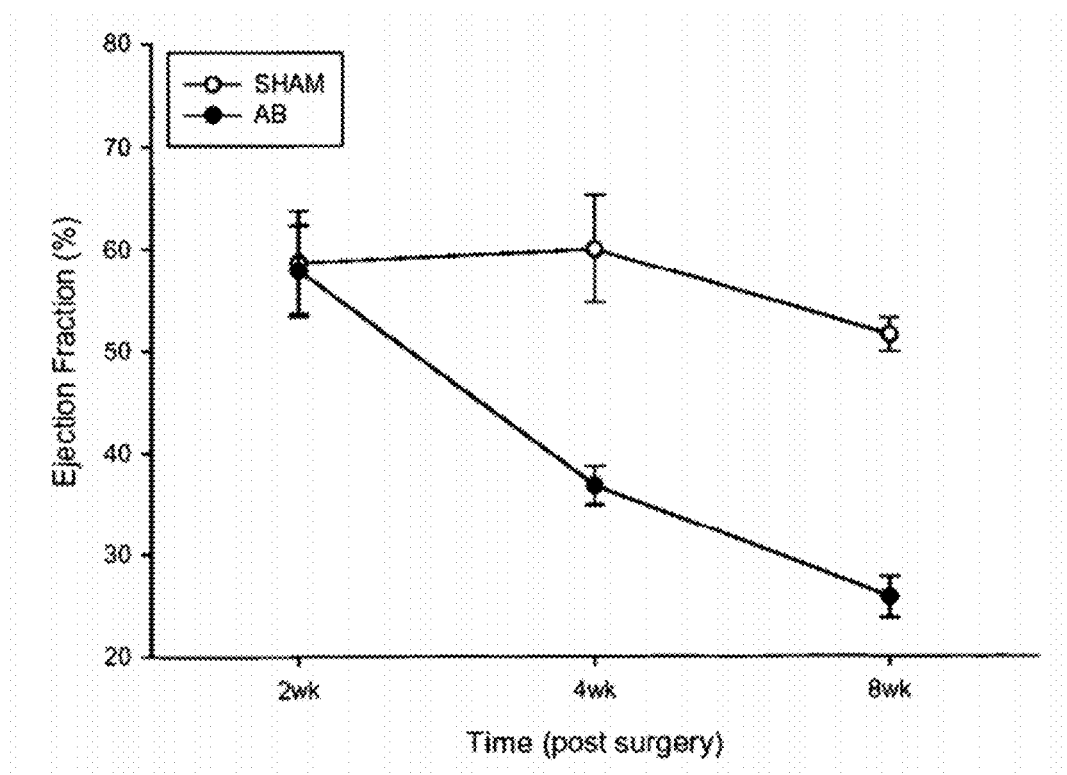
FIG. 2B is a graph depicting the change in the left ventricular ejection fraction at 2, 4, and 8 weeks post-surgery, as determined by echocardiograph and hemodynamic parameters, from wild type and AB mice (closed circles indicate the data from sham operated mice and open circles indicate the data from mice with aortic binding (AB))

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate exemplary embodiments of the disclosure, in one form, and such exemplifications are not to be construed as limiting the scope of the disclosure in any manner.

BRIEF DESCRIPTION OF THE SEQUENCE LISTING

SEQ ID NO.: 1 is a 289 amino acid sequence for a mimecan protein.

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

As disclosed herein, a mimecan marker for the assessment and, in some cases, diagnosis of heart failure ("HF") is provided. Additionally, a combination of markers including a mimecan marker for the assessment and, in some cases, diagnosis of HF is provided.

According to a first embodiment of the present disclosure, a method for assessing HF in an individual comprising the steps of: a) measuring in a sample obtained from the individual the concentration of the mimecan marker; b) optionally measuring in the sample the concentration of one or more other marker(s) of HF; and c) assessing HF by comparing the concentration determined in step (a) and optionally the concentration(s) determined in step (b) to the "control" concentration of this marker (or these markers) as established in a control sample (or a population of control samples).

As used herein, each of the following terms has the meaning associated with it in this section.

The articles "a" and "an" are used herein to refer to one, or more than one (i.e., at least one), of the grammatical object of the article. By way of example, "an antibody" means one antibody or more than one antibody.

The expression "one or more" denotes approximately 1 to 50.

The term "marker" or "biochemical marker" as used herein refers to a molecule to be used as a target for analyzing a patient's test sample. In one embodiment examples of such molecular targets are proteins or polypeptides. Proteins or polypeptides used as a marker in the present disclosure are contemplated to include naturally occurring fragments of said protein in particular, immunologically detectable fragments. Immunologically detectable fragments may comprise at least 6, 7, 8, 10, 12, 15 or 20 contiguous amino acids, for example, of said marker polypeptide. One of skill in the art would recognize that proteins which are released by cells, or present in the extracellular matrix, may be damaged, for example during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present disclosure. In addition, or in the alternative a marker polypeptide may carry a post-translational modification. Examples of post-translational modifications amongst others are glycosylation, acylation, and/or phosphorylation.

The term "assessing heart failure" is used to indicate that the method according to the present disclosure will aid the physician to assess whether an individual is at risk of developing HF, or aid the physician in the assessment of a HF patient in one, or several, other areas of diagnostic relevance in HF. Exemplary areas of diagnostic relevance in assessing an individual with HF include the staging of HF, differential diagnosis of acute and chronic HF, judging the risk of disease progression, guidance for selecting an appropriate drug, monitoring of response to therapy, and the follow-up of HF patients.

A "marker of heart failure" as referred to in the present disclosure is a marker that, if combined with the marker mimecan, adds relevant information in the assessment of HF and the diagnostic question under investigation. The information is considered relevant or of additive value if at a given specificity the sensitivity, or if at a given sensitivity the specificity, for the assessment of HF can be improved by including said marker into a marker combination already comprising the marker mimecan. The improvement in sensitivity or specificity, respectively, is statistically significant at a level of significance of $p=0.05, 0.02, 0.01$ or lower, for example. According to an embodiment of the instant disclosure, the one or more other markers of HF may be selected from the group consisting of a natriuretic peptide marker, a cardiac troponin marker, and a marker of inflammation.

As described herein, the natriuretic peptide family, including the atrial natriuretic peptide family and the brain natriuretic peptide family may be of value in the assessment of HF. Furthermore, B-type natriuretic peptide markers may provide a tool useful according to the instant application for monitoring disease progression in patients with HF and for assessing their risk of cardiovascular complications, such as a heart attack.

The term "sample" as used herein refers to a biological sample obtained for the purpose of evaluation in vitro. According to the methods disclosed herein, the sample or patient sample may comprise any body fluid. Exemplary test samples include blood, serum, plasma, urine, saliva, and synovial fluid, for example. Additionally, samples may include whole blood, serum, plasma or synovial fluid. Plasma and/or serum are generally considered the most convenient types of samples. Further, such assessments are generally made in vitro and the patient sample is usually discarded following analysis (e.g., the material of the patient sample is not transferred back into the patient's body). Furthermore, although not required, the sample is typically a liquid sample (e.g., whole blood, serum, or plasma).

A person of skill in the art will understand that the expression "comparing the concentration . . . to the concentration as established in a control sample" refers to assessment of one or more concentrations in (one or more) test samples and comparing those values to one or more concentrations in (one or more) control samples. The control sample may be an internal or an external control sample. In one embodiment an internal control sample is used, i.e. the marker level(s) is(are) assessed in the test sample as well as in one or more other sample(s) taken from the same subject to determine if there are any changes in the level(s) of the assessed marker(s). In another embodiment an external control sample is used. For an external control sample the presence or amount of a marker in a sample derived from the individual is compared to its presence or amount in another individual whom, for example, may be known to suffer from, or known to be at risk of, a given condition. Additionally, the control sample may come from "another" individual or population of individuals known to be free of a given condition, i.e., a "normal individual". For example, a marker level in a patient sample can be compared to a level known to be associated with a specific course of disease in HF. Usually the sample's marker level is directly or indirectly correlated with a diagnosis and the marker level is e.g.

used to determine whether an individual is at risk for HF. Alternatively, the sample's marker level can e.g. be compared to a marker level known to be associated with a response to therapy in HF patients, the differential diagnosis of acute and chronic HF, the guidance for selecting an appropriate drug to treat HF, in judging the risk of disease progression, or in the follow-up of HF patients. Depending on the intended diagnostic use an appropriate control sample may be chosen, and a control or reference value for the marker established therein.

It should be appreciated that such control sample in one embodiment may be obtained from a reference population that is age-matched and free of confounding diseases. In general, according to the present disclosure, healthy or "normal individuals" (as described above) comprise a reference population for establishing control values. As also should be appreciated, the marker values established in a control sample may be dependent on the assay used. For example, samples from 100 well-characterized individuals (from an appropriate reference population) may be used to establish a control (reference) value. Additionally, it should be understood that the reference population may consist of approximately 20, 30, 50, 200, 500 or 1000 individuals, or any value therebetween.

As explained above, HF is a major and growing public health problem which is characterized by a loss in the heart's ability to pump as much blood as the body needs. HF is a complex disease in which, during the early phases of HF, damage to the heart caused by this disease is generally present and ongoing while the patient remains asymptomatic.

Known pathophysiological changes which occur in HF include: (i) activation of the hypothalamic-pituitary-adrenal axis; (ii) systemic endothelial dysfunction; and (iii) myocardial remodeling.

Therapies aimed at counteracting the activation of the hypothalamic-pituitary-adrenal axis include beta-adrenergic blocking agents (B-blockers), angiotensin converting enzyme (ACE) inhibitors, certain calcium channel blockers, nitrates and endothelin-1 blocking agents. Calcium channel blockers and nitrates, while producing clinical improvement have not been clearly shown to prolong survival, whereas B-blockers and ACE inhibitors have been shown to prolong life, as have aldosterone antagonists. Experimental studies using endothelin-1 blocking agents have shown a beneficial effect.

Systemic endothelial dysfunction is a well-recognized feature of HF and is clearly present by the time signs of left ventricular dysfunction are present. Endothelial dysfunction is important with respect to the intimate relationship of the myocardial microcirculation with cardiac myocytes. Evidence suggests that microvascular dysfunction contributes significantly to myocyte dysfunction and the morphological changes which lead to progressive myocardial failure.

In terms of underlying pathophysiology, evidence suggests that endothelial dysfunction may be caused by a relative lack of NO which can be attributed to an increase in vascular $O_2$-formation by an NADH-dependent oxidase and subsequent excess scavenging of NO. Potential contributing factors to increased $O_2$-production include increased sympathetic tone, norepinephrine, angiotensin II, endothelin-1 and TNF-α. In addition, levels of IL-10, a key anti-inflammatory cytokine, are inappropriately low in relation to TNF-α levels. It is now believed that elevated levels of TNF-α, with associated proinflammatory cytokines including IL-6, and soluble TNF-α receptors, play a significant role in the evolution of HF by causing decreased myocardial contractility, biventricular dilatation, and hypotension and are probably involved in endothelial activation and dysfunction. It is also believed that TNF-α may play a role in the hitherto unexplained muscular wasting which occurs in severe HF patients. Preliminary studies in small numbers of patients with soluble TNF-receptor therapy have indicated improvements in NYHA functional classification and in patient well-being, as measured by quality of life indices.

Myocardial remodeling is a complex process which accompanies the transition from asymptomatic to symptomatic HF, and may be described as a series of adaptive changes within the myocardium, like alterations in ventricular shape, mass and volume. The main components of myocardial remodeling are alterations in myocyte biology, like myocyte hypertrophy, loss of myocytes by necrosis or apoptosis, alterations in the extracellular matrix and alterations in left ventricular chamber geometry. It is currently unclear whether myocardial remodeling is simply the end-organ response that occurs following years of exposure to the toxic effects of long-term neurohormonal stimulation, or whether myocardial remodeling contributes independently to the progression of HF. Current evidence suggests appropriate therapy can slow or halt progression of myocardial remodeling.

As indicated above, myocyte hypertrophy is likely to represent one of the first steps down the road to HF. Myocyte hypertrophy is characterized in-part by an increased expression of some genes encoding contractile proteins, such as β-myosin heavy chain and troponin T (TnT), and of some non-contractile proteins, such as A-type and B-type natriuretic peptides, by an increased cell size, and by cytoskeletal alteration.

Studies of human and animal models suggest depressed myocyte function in the later stages of cardiac failure. The mechanisms that underlie myocyte dysfunction have been suggested to involve alterations in the calcium-handling network, myofilament and cytoskeleton. For example, in human and animal models, sarcoplasmic reticulum calcium-ATPase enzyme activity has been shown to be reduced, while both mRNA and protein levels of the sarcolemmal Na+/Ca2+ exchanger have been shown to be increased. Moreover, isoform-switching of TnT, reduced phosphorylation of troponin I (TnI), decreased myofibrillar actomyosin ATPase activity, and enhanced microtubule formation in both human and animal models of HF have also been indicated.

Initially the changes to the heart, leading to myocardial remodeling, are meant to compensate for the diseased parts of the myocardium in order to sustain the body's demand for oxygen and nutrients. However, the compensatory phase of HF is limited, and, ultimately, the failing heart is unable to maintain cardiac output adequate to meet the body's needs. Thus, there is a transition from a compensatory phase to a decompensatory phase. In the decompensatory phase, the cascade of changes in the heart continues but is no longer beneficial, moving the patient down the progression of HF to a chronic state and eventual death.

According to the "ACC/AHA 2005 Guideline Update for the Diagnosis and Management of Chronic Heart Failure in the Adult" (reported at www.acc.org) the disease continuum in the area of HF is nowadays grouped into four stages as noted above. In stages A and B the individuals at risk of developing HF are found, whereas stages C and D represent the groups of patients showing signs and symptoms of HF. The details for defining these different stages, A through D, as provided in the above reference are hereby incorporated by reference in their entirety.

Mimecan.

Mimecan is a small proteoglycan with leucin-rich repeats and a precursor consisting of 298 amino acids (SEQ ID NO: 1). Other names of mimecan are OGN, osteoglycin, DKFZp586P2421, OG, OIF, SLRR3A.

Mimecan is a member of the secreted small leucine rich proteoglycans (SLRP) family with structurally related core proteins. A common feature shared by all SLRPs is the tandem leucine-rich repeat (LRR) units in the C-terminal half of the core protein. In the N-terminal region, however, each class of SLRP has a unique domain containing a cysteine cluster with conserved spacing called the LRR N-domain. Class III SLRPs contain six carboxyl LRRs and include mimecan, epiphycan, and opticin.

Studies of mouse knockouts for class I and II members, such as decorin, biglycan, lumecan and fibromodulin, have shown that the SLRP-deficient mice displayed a wide array of defects attributable to abnormal collagen fibrillogenesis suggesting that these SLRPs play roles in establishing and maintaining the collagen matrix. Deficiency of class III mimecan was also shown to contribute to collagen fibril abnormalities.

Mimecan is a multifunctional component of the extracellular matrix. It binds to a variety of other proteins (IGF2, IKBKG, IFNB1, INSR, CHUK, IKBKB, NFKBIA, ID 5, Cd3, retinoic acid, APP, TNF, lipopolysaccharide, c-abl oncogene 1, receptor tyrosine kinase, v-crk sarcoma virus CT10 oncogene, v-src sarcoma viral oncogene). These diverse binding activities may account for the ability of mimecan to exert diverse functions in various tissues.

Mimecan has been found in cornea, bone, skin and further tissues. Its expression pattern is altered in different pathological conditions. Mimecan has also been shown to be involved in regulating collagen fibrillogenesis, a process essential in development, tissue repair, and metastasis. It has also been shown to play a role in bone formation in conjunction with TGF-beta-1 or TGF-beta-2. Additionally, mimecan was found to be constitutively expressed in mouse lens.

Mimecan was shown to be up-regulated after vascular injury and after low-laser irradiation of osteoblasts indicating that the corresponding protein may play a role in wound healing in vascular smooth muscle cells and in osteoblasts. Additionally, mimecan was found to be upregulated in activated endothelium and to possibly play a role in atherosclerosis. Mimecan was also found to be expressed at low levels or not at all in most cancer cell lines (down regulated in colorectal cancer (CRC), as compared to normal mucosa). WO 2006/043031, which is hereby incorporated by reference in its entirety, relates to the use of a therapeutic agent that may promote mimecan activity for the prevention or treatment of cancer. Despite the above information regarding the biological role of mimecan, however, its function is still not clear.

The present disclosure provides and demonstrates that, in accordance with the methods disclosed herein, an increased value for mimecan, as measured from a bodily fluid sample derived from an individual, is diagnostically useful in assessing HF.

According to the present disclosure, the values for mimecan (as measured in a control group or a control population) are, for example, used to establish a cut-off value or a reference range. A value above such cut-off value or outside the reference range at its higher end is considered as elevated.

In a one embodiment a fixed cut-off value may be established. Such cut-off value may be chosen to match the diagnostic question of interest, for example.

In one embodiment values for mimecan as measured in a control group or a control population are used to establish a reference range. In some embodiments, a mimecan concentration is considered as elevated if the value measured is above the 90%-percentile of the reference range. In some embodiments a mimecan concentration is considered as elevated if the value measured is above the 95%-percentile, the 96%-percentile, the 97%-percentile, or the 97.5%-percentile of the reference range.

In some embodiments the control sample may be an internal control sample. In such embodiments, serial samples may be obtained from the individual under investigation and the marker levels may be compared. This may, for example, be useful in assessing the efficacy of therapy.

According to a method disclosed herein, a liquid sample may be obtained from an individual and the concentration of mimecan in such sample is measured. An "individual," as used herein, may refer to a human or non-human organism. Thus, the methods and compositions described herein are applicable to both human and veterinary disease.

According to exemplary embodiments provided herein, the marker mimecan is measured from a liquid sample by use of a specific binding agent. A specific binding agent may include a receptor for mimecan, a lectin binding to mimecan, or an antibody to mimecan. According to the instant disclosure, a specific binding agent may have at least an affinity of $10^7$ l/mol for its corresponding target molecule. In some embodiments the specific binding agent may have an affinity of $10^8$ l/mol or $10^9$ l/mol for its target molecule. As should be understood by a person of skill in the art, the term "specific" as used herein indicates that other biomolecules present in the sample do not bind to the binding agent specific for mimecan with greater affinity or preference. The level of binding to a biomolecule other than the target molecule results in a binding affinity which is 10% or less, or preferably only 5% or less, of the affinity to the target molecule, for example. According to some embodiments, preferred specific binding agents will, in some cases, fulfill both of the above criteria for affinity as well as for specificity.

According to some embodiments of the instant disclosure, specific binding agents may be an antibody which is reactive with mimecan. The term antibody may refer to a polyclonal antibody, a monoclonal antibody, antigen binding fragments of such antibodies, single chain antibodies, as well as to genetic constructs comprising the binding domain of an antibody.

Any antibody fragment retaining the above criteria of a specific binding agent may be used. Antibodies may be generated by state of the art procedures, such as described in Tijssen (Tijssen, P., Practice and theory of enzyme immunoassays, Elsevier Science Publishers B.V., Amsterdam (1990), the whole book, especially pages 43-78). Additionally, methods based on immunosorbents can be used for the specific isolation of antibodies in order that the quality of polyclonal antibodies, and hence their performance in immunoassays can be enhanced.

According to embodiments disclosed herein, polyclonal antibodies raised in goats may be used. However, it should be understood that polyclonal antibodies from different species such as rats, rabbits or guinea pigs, as well as monoclonal antibodies can be used. Since monoclonal antibodies can be produced in any amount required with constant properties, they can provide useful tools in development of an assay for clinical routine.

According to another embodiment of the present disclosure, the generation and the use of monoclonal antibodies to mimecan in a method according to the present disclosure is provided.

According to the instant disclosure, recombinant production of mimecan may be used to obtain higher amounts of mimecan (as compared to purification from a natural source), although mimecan from a natural source is within the scope of the instant disclosure. In an embodiment of the instant disclosure, mimecan is produced by recombinant expression using an eukaryotic expression system. Exemplary eukaryotic expression systems include baculovirus expression, expression in yeast and expression in a mammalian expression system. In some embodiments the expression of mimecan may be performed in a mammalian expression system. Exemplary mammalian expression systems include CHO cells, HEK cells, myeloma cells, etc. In further embodiments, a recombinantly produced mimecan may be used as an antigen in the production of poly- or monoclonal antibodies against mimecan. Further, polyclonal antibodies may be purified by immunoadsorption over an mimecan immunoadsorber making use of recombinantly produced mimecan as described herein above.

It should be understood that alternative strategies for generating antibodies, as are known in the art, may also be used in accordance with the present disclosure. Such strategies may comprise amongst others, the use of synthetic or recombinant peptides, representing a clinically relevant epitope of mimecan for immunization. Alternatively, DNA immunization also known as DNA vaccination may be used, for example.

According to the instant disclosure, a liquid sample obtained from an individual is incubated with a specific binding agent for mimecan under conditions appropriate for formation of a binding agent mimecan-complex (such incubation binding conditions will generally be standard conditions for the art). The amount of binding agent mimecan-complex is measured and used in the assessment of HF. As the skilled artisan will appreciate there are numerous methods to measure the amount of the specific binding agent mimecan-complex, for example, as described in detail in Tijssen or Diamandis, E. P. and Christopoulos, T. K. (eds.), Immunoassay, Academic Press, Boston (1996).

In some embodiments, mimecan may be detected in a sandwich type assay format. In such assay a first specific binding agent is used to capture mimecan on the one side and a second specific binding agent, which is labeled to be directly or indirectly detectable, is used on the other side. Such embodiments may be qualitative (mimecan present or absent) or quantitative (amount of mimecan is determined) immunoassays.

As is described in further detail in the Examples section, two mouse models were used to identify mRNA and polypeptides found in heart tissue of experimental animals by advanced microarray and proteomics methods. These models yielded at least partially conflicting data, and, of course tissue data for the mRNA or the respective polypeptides are not representative to the presence or absence of these polypeptides in the circulation. A marker found to be differentially expressed in one model may not be differentially expressed in a second model or even show conflicting data in yet a further model. Differentially expressed mRNA may be found not to correlate to enhanced levels of the respective polypeptide in the circulation. Even if a protein may be differentially expressed in tissue this protein in most cases is not of any diagnostic relevance if measured from a bodily fluid, because it may not be released to the circulation, may become fragmented or modified, e.g., upon release from a cell or tissue, may not be stable in the circulation, may not be measurable in the circulation, may not be specific for a given disease, etc.

However, the instant disclosure presents the surprising advancement in being able to detect protein mimecan in a bodily fluid sample. Even more surprising, the disclosure discloses the ability to demonstrate that the presence of mimecan in such liquid samples obtained from an individual can be correlated to HF. Furthermore, as disclosed herein, no tissue and no biopsy sample is required to make use of the marker mimecan in the assessment of HF. As will be obvious to a person of skill in the art, measuring the level of protein mimecan is advantageous in the field of HF.

An embodiment of the present disclosure provides a method for assessing HF in an individual comprising the steps: (a) measuring in a sample obtained from the individual the concentration of the marker mimecan, wherein said sample is a body fluid sample; (b) optionally measuring in the sample the concentration of one or more other marker(s) of HF selected from the group consisting of a natriuretic peptide marker, a cardiac troponin marker, and a marker of inflammation; and (c) assessing HF by comparing the concentration determined in step (a) and optionally the concentration(s) determined in step (b) to the concentration of this marker or these markers as established in a control sample, wherein an increased concentration of mimecan is indicative of HF.

In some embodiments the method according to the present disclosure is practiced with serum as a liquid sample material. In other embodiments the method according to the present disclosure is practiced with plasma as liquid sample material. In other embodiments the method according to the present disclosure is practiced with whole blood as liquid sample material.

In some embodiments of the present disclosure, use of protein mimecan as a marker molecule in the assessment of HF from a liquid sample obtained from an individual is provided.

According to some embodiments of the instant disclosure, a single event or process may cause the respective disease, for example in some infectious diseases. In other cases correct diagnosis can be very difficult, especially when the etiology of the disease is not fully understood as is the case of HF. As person of skill in the art will appreciate, no biochemical marker in the field of HF will be diagnostic with 100% specificity and at the same time 100% sensitivity for a certain diagnostic question. Rather, as person of skill in the art will appreciate, biochemical markers are used to assess with a certain likelihood or predictive value an underlying diagnostic question. The skilled artisan is fully familiar with the mathematical/statistical methods that routinely are used to calculate a relative risk or likelihood for the diagnostic question to be assessed. In routine clinical practice, various clinical symptoms and biological markers are generally considered together by a physician in the diagnosis, treatment, and management of the underlying disease.

In further embodiments of the present disclosure, the method for assessment of HF is performed by measuring the concentration of mimecan and of one or more other markers and by using the concentration of mimecan and of the one or more other markers in the assessment of HF.

In the assessment of HF, the marker mimecan will aid the physician in one or more of the following aspects: assessment of an individual's risk for HF and/or assessment of a patient having HF (for example, identification of the stage of HF for differentiating between acute and chronic HF, judging the risk of disease progression, providing guidance in selecting an appropriate therapy, monitoring a patient's response to therapy, and monitoring the course of disease, for example, in the follow-up of HF patients).

Screening (Assessment of Whether Individuals May be at Risk for Developing HF).

An embodiment of the present disclosure relates to an in vitro method for assessing whether an individual is at risk for developing HF comprising the steps of measuring in a sample the concentration of the marker mimecan, optionally measuring in the sample the concentration of one or more other marker(s) of HF, and assessing said individual's risk for developing HF by comparing the concentration for mimecan and optionally the concentration(s) determined for the optionally one or more other marker(s) to the concentration of this marker or these markers to its or their reference value(s).

Screening in the sense of the present disclosure relates to the unbiased assessment of individuals regarding their risk for developing HF. Whereas such screening may in theory be performed on any sample, in clinical practice such screening option will usually be given to individuals somehow at risk for development of HF. As discussed above, such individuals may clinically be asymptomatic (e.g., they may have no signs or symptoms of HF). In one preferred embodiment screening for HF may be given to individuals at risk of developing HF (for example, individuals falling into the stages A or B as defined by the ACC/AHA practice guidelines described above).

As mentioned above, HF is one of the most prevalent, costly and life-threatening diseases in developed countries. Because of its high prevalence and its long asymptomatic phase, identification of individuals at risk for developing HF would be valuable for intervention and, if possible, for interrupting the progression of the disease. Without an early risk assessment, prevention of disease progression from the asymptomatic state into a symptomatic phase of HF appears potentially impossible.

According to the instant disclosure, the risk for HF may be assessed by mathematical/statistical methods which a person of the skill in the art will appreciate. Preferably an individual's risk for HF is expressed in relative terms, and given as a relative risk (RR). In order to calculate RR for HF, an individual's value for mimecan is compared to the values established for mimecan in a reference population, preferably healthy individuals not developing HF. Also, at least in some embodiments, the assessment of such RR for HF is based on a group of individuals that have developed HF within the study period, for example within one or two years, and a group of individuals that did not develop HF in the same study period.

In another embodiment the present disclosure relates to the use of the marker mimecan in the screening for HF. As the skilled artisan will appreciate the term "use as a marker" implies that the concentration of a marker molecule is quantified by appropriate means and that value measured for such marker is then used to indicate, i.e. to mark, the presence or absence of a disease or clinical condition. Appropriate means for quantitation for example are specific binding agents, like antibodies.

The screening for HF may be performed in individuals suspected to be at risk of future HF. Patients at risk of future HF in this sense may comprise patients diagnosed with hypertension, atherosclerotic disease, diabetes, obesity and metabolic syndrome, for example. As such, the risk for future HF may be assessed with individuals suffering from hypertension, atherosclerotic disease, diabetes, and/or metabolic syndrome, for example.

Also, the use of the marker mimecan in assessing the risk for future HF for an individual in stage B according to the ACC/AHA practice guidelines (e.g., an individual exhibiting a structural change at the heart but not showing symptoms of HF) is also provided and disclosed. In further embodiments the present disclosure relates to the use of mimecan as one marker of a HF marker combination for HF screening purposes.

According to the instant disclosure, in a screening setting, an elevated level of mimecan presents a positive indicator for an individual's increased risk to develop H F.

Staging of Patients.

An embodiment of the present disclosure provides an in vitro method aiding in the staging of HF patients, comprising the steps of: a) measuring in a sample the concentration of the marker mimecan; b) optionally measuring in the sample the concentration of one or more other marker(s) of HF; and staging HF by comparing the concentration determined in step a) and optionally the concentration(s) determined in step b) to the concentration of this marker or these markers to its or their reference value(s). In some embodiments, the level of marker mimecan may be used as an aid in classifying the individuals investigated into groups, for example a group of individuals that are clinically "normal" (i.e., individuals in stage A according to the ACA/ACC classification), a group that are asymptomatic patients having structural heart disease (stage B according to the ACA/ACC classification), and a group of patients having HF (i.e., patients in stage C or stage D according to the ACA/ACC classification).

Differentiation Between an Acute Cardiac Event and Chronic Cardiac Disease.

According to some embodiments of the instant disclosure, the present disclosure relates to an in vitro method aiding in the differential diagnosis between an acute cardiac event and chronic cardiac disease, comprising the steps of measuring in a sample the concentration of the marker mimecan, optionally measuring in the sample the concentration of one or more other marker(s) of HF, and establishing a differential diagnosis between an acute cardiac event and chronic cardiac disease by comparing the concentration determined in the measuring step and optionally the concentration(s) determined in the optionally measuring step, to the concentration of this marker or these markers to its or their reference value(s).

An "acute cardiac event" relates to an acute condition, disease or malfunction of the heart, particularly to acute HF, e.g., myocardial infarction (MI) or arrhythmia. Depending on the extent of an MI, it may be followed by LVD and CHF.

Generally, "chronic cardiac disease" is a weakening of heart function, for example, due to ischemia of the heart, coronary artery disease, or previous, particularly small, myocardial infarction(s) (possibly followed by progressing LVD). According to the instant disclosure, it may also be a weakening due to inflammatory diseases, heart valve defects (e.g., mitral valve defects), dilatative cardiomyopathy, hypertrophic cardiomyopathy, heart rhythm defects (arrhythmias), and chronic obstructive pulmonary disease. It should also be appreciated that chronic cardiac disease may also include patients who have suffered from an acute coronary syndrome, e.g., MI, but who are presently not suffering from an acute cardiac event.

According to the instant disclosure, acute cardiac events and chronic cardiac disease are differentiated because each may require different treatment regimens. For example, for a patient presenting with acute myocardial infarction early treatment for reperfusion may be of utmost importance. Whereas a treatment for reperfusion performed on a patient with chronic HF at best is of no or only little harm to this patient.

In a further embodiment according to the present disclosure the marker mimecan is used in the differential diagnosis of acute and chronic HF.

Assessing the Risk of Disease Progression.

An embodiment of the present disclosure relates to an in vitro method for assessing an HF-patient's risk for disease progression, comprising the steps of measuring in a sample the concentration of the marker mimecan, optionally measuring in the sample the concentration of one or more other marker(s) of HF, and establishing said individual's risk for disease progression by comparing the concentration for mimecan and optionally the concentration(s) determined for the optionally one or more other marker(s) to the concentration of this marker or these markers to its or their reference value(s).

At present it is very difficult to assess and/or predict (with a reasonable likelihood) whether a patient diagnosed with HF has a more or less stable status and if the disease will progress and the patient's health status as result is likely to worsen. Severity and progression of HF is usually established clinically by assessing the clinical symptoms or by identification of adverse changes by using imaging technologies such as echocardiography. In one embodiment the worsening of HF is established by monitoring the left ventricular ejection fraction (LVEF). Deterioration in LVEF by 5% or more is considered as disease progression.

In another embodiment, the present disclosure therefore relates to the use of the marker mimecan in assessing the risk of disease progression for a patient suffering from HF. In the assessment of disease progression for patients suffering from HF an elevated level of mimecan is an indicator for an increased risk of disease progression.

Guidance in Selecting an Appropriate HF Therapy.

In another embodiment the present disclosure relates to an in vitro method, aiding in the selection of an appropriate HF-therapy, comprising the steps of measuring in a sample the concentration of the marker mimecan, optionally measuring in the sample the concentration of one or more other marker(s) of HF, and selecting an appropriate therapy by comparing the concentration for mimecan and optionally the concentration(s) determined for the optionally one or more other marker(s) to the concentration of this marker or these markers to its or their reference value(s).

It is expected that the marker mimecan will be of help in aiding the physician to select the most appropriate treatment regimen from the various treatment regimens at hand in the area of HF. Further embodiments therefore relate to the use of the marker mimecan in selecting a treatment regimen for a patient suffering from HF.

Monitor a Patient's Response to Therapy.

Embodiments of the present disclosure relate to in vitro methods for monitoring a patient's response to HF-therapy, comprising the steps of: a) measuring in a sample the concentration of the marker mimecan; b) optionally measuring in the sample the concentration of one or more other marker(s) of HF, and of monitoring a patient's response to HF-therapy by comparing the concentration determined in step a) and optionally the concentration(s) determined in step b) to the concentration of this marker or these markers to its or their reference value(s).

The above method for motoring a patient's response to therapy may be practiced by establishing the pre- and post-therapeutic marker level for mimecan and for the optionally one or more other marker(s) and by comparing the pre- and the post-therapeutic marker level(s).

Currently, the diagnosis of HF is clinically established. As described above, HF is considered clinically established if a patient meets the criteria of stages C or D as defined by the ACC/AHA practice guidelines. According to these guidelines, stage C includes patients with structural heart disease and with prior or current symptoms of HF. Patients in stage D have refractory HF that requires specialized interventions.

However, as described herein the marker mimecan presents an appropriate marker for monitoring a patient's response to therapy. As such, the present disclosure also relates to the use of mimecan in monitoring a patient's response to therapy. Further, the marker mimecan may also be used for establishing a baseline value before therapy and to measure mimecan at one time-point or several time-points after therapy. In the follow-up of HF patients a reduced level of mimecan is a positive indicator for an effective treatment of HF.

Marker Combination.

Further embodiments of the instant disclosure include the determination of biochemical markers, individually or measured in combination. According to some embodiments, combinations of markers are measured simultaneously using a chip- or a bead-based array technology. The concentrations of the biomarkers are then interpreted independently, for example using an individual cut-off for each marker, or the concentrations are combined for interpretation (e.g., they form a marker combination).

As a skilled artisan will appreciate, a marker level may be correlated to a certain likelihood or risk in various ways. For example, and within the scope of the instant disclosure, the values measured for the marker mimecan and the one or more other marker(s) are mathematically combined and the combined value is correlated to the underlying diagnostic question. Marker values may be combined with the measurement of mimecan by any appropriate state of the art mathematical method.

According to some embodiments of the instant disclosure, the mathematical algorithm applied in the combination of markers may be a logistic function. The result of applying such mathematical algorithm or such logistical function may be a single value. Dependent on the underlying diagnostic question such value may easily be correlated to the risk of an individual for HF, or to other intended diagnostic uses helpful in the assessment of patients with HF, for example. In another manner, such logistic function may be obtained by: a) classification of individuals into the groups (e.g., normal individuals, at risk individuals for HF, patients with acute or chronic HF, etc.); b) identification of markers which differ significantly between these groups by univariate analysis; c) logistic regression analysis to assess the independent discriminative values of markers useful in assessing these different groups; and d) construction of the logistic function to combine the independent discriminative values. In such types of analysis, the markers are no longer independent but represent a marker combination.

In some embodiments, the logistic function used for combining the values for mimecan and the value of at least one further marker may be obtained by: a) classification of individuals into the groups of normals and individuals at risk of HF; b) establishing the values for mimecan and the value of the at least one further marker; c) performing logistic regression analysis; and d) construction of the logistic function to combine the marker values for mimecan and the value of the at least one further marker.

A logistic function for correlating a marker combination to a disease preferably employs an algorithm developed and obtained by applying statistical methods. Appropriate statistical methods include, for example, Discriminant analysis (DA) (e.g., linear-, quadratic-, regularized-DA), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks, and Genetic Algorithms based Methods. An appropriate statistical method may be selected in order to evaluate a marker combination of the present disclosure and thereby to obtain an appropriate mathematical algorithm. The statistical method employed to obtain the mathematical algorithm used in the assessment of HF may also be selected from DA (e.g., Linear-, Quadratic-, Regularized Discriminant Analysis), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression). Details relating to these statistical methods may be found in the following references which are hereby incorporated by reference in their entirety: Ruczinski, I., et al., J. of Computational and Graphical Statistics 12 (2003) 475-511; Friedman, J. H., J. of the American Statistical Association 84 (1989) 165-175; Hastie, T., et al., The Elements of Statistical Learning, Springer Verlag (2001); Breiman, L., et al., Classification and regression trees, Wadsworth International Group, California (1984); Breiman, L., Machine Learning 45 (2001) 5-32; Pepe, M. S., The Statistical Evaluation of Medical Tests for Classification and Prediction, Oxford Statistical Science Series, 28, Oxford University Press (2003); and Duda, R. O., et al., Pattern Classification, John Wiley & Sons, Inc., 2nd ed. (2001).

It is a preferred embodiment of the disclosure to use an optimized multivariate cut-off for the underlying combination of biological markers and to discriminate state A from state B, e.g., normals and individuals at risk for HF, HF patients responsive to therapy and therapy failures, patients having an acute HF and HF patients having chronic heart failure, HF patients showing disease progression and HF patients not showing disease progression, respectively.

The area under the receiver operator curve (=AUC) is an indicator of the performance or accuracy of a diagnostic procedure. Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

In generally the clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example, health and disease or disease progression versus no disease progression.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results)/(number of true-positive + number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative + number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1—specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot (AUC). By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

The overall assay sensitivity depends on the specificity required for practicing the method disclosed here. In some settings a specificity of 75% may be sufficient and statistical methods and resulting algorithms can be based on this specificity requirement. In some embodiments the method used to assess individuals at risk for HF is based on a specificity of 80%, of 85%, or also of 90% or of 95%.

As discussed above, the marker mimecan aids in assessing an individual's risk of developing HF as well as in the further in vitro diagnostic assessment of a patient having HF. An embodiment accordingly is the use of mimecan as a marker molecule in the assessment of HF.

The use of a marker combination comprising mimecan and one or more other marker(s) of HF in the assessment of HF patients or in the assessment of individuals at risk for HF represents a further preferred embodiment of the present disclosure. In such marker combination according to the instant disclosure, the one or more other marker(s) may be selected from the group consisting of a natriuretic peptide marker, a cardiac troponin marker, and a marker of inflammation.

The one or more selected other HF marker(s) with which the measurement of mimecan may be combined may be selected from the group consisting of a natriuretic peptide marker, a cardiac troponin marker, and a marker of inflammation. These exemplary other markers whose measurement(s) may be combined with the measurement of mimecan or which form part of the HF marker combination comprising mimecan, respectively, are discussed in more detail below.

Natriuretic Peptide Marker.

As explained above, embodiments of the instant disclosure include an HF marker combination comprising mimecan and at least one further marker, for example, a natriuretic peptide marker. According to the instant disclosure, a natriuretic peptide marker comprises a marker selected from the atrial natriuretic peptide (ANP) family or the brain natriuretic peptide (BNP) family.

The polypeptide markers in either the ANP family or the BNP family may be derived from the preproforms of the corresponding active hormones.

Exemplary natriuretic peptide markers according to the present disclosure include NT-proANP, ANP, NT-proBNP, BNP, and immunologically detectable physiological fragments thereof. As the skilled artisan readily appreciates, the immunologically detectable fragment has to comprise at least one epitope allowing for the specific detection of such physiological fragment. A physiological fragment is a fragment in which the epitope is as naturally present in an individual's circulation.

The markers in both the natriuretic peptide families represent fragments of the corresponding pro-hormones, i.e., proANP and proBNP, respectively. Since similar considerations apply for both families, only the BNP marker family shall be described in some detail. The pro-hormone of the BNP family, i.e., proBNP consists of 108 amino acids. proBNP is cleaved into the 32 C-terminal amino acids (77-108) representing the biologically active hormone BNP and the N-terminal amino acids 1-76 called N-terminal proBNP (or NT-proBNP). BNP, N-terminal proBNP (1-76) as well as further breakdown products circulate in blood. Whether the complete precursor molecule (proBNP 1-108) also occurs in the plasma is not completely resolved. It is however described that at least a low release of proBNP (1-108) in plasma is detectable and that in some cases due to quick partial breakdown at the N-terminal end, some amino acids are absent. Today it is generally accepted that for NT-proBNP, the central portion of the molecule, residing in between the amino acids 10 to 50 represents a rather physiologically stable part. NT-proBNP (1-16) molecules comprising this central part of NT-proBNP can be reliably measured from bodily fluids. Methods relating to the immunological detection of this central part of the NT-proBNP molecule are provided in WO 00/45176, the disclosure of which is hereby incorporated by reference in its entirety. Additionally, it is also within the scope of the present disclosure, and may be of advantage in some settings to measure only a certain subfraction of NT-proBNP for which the term native NT-proBNP has been proposed. Detailed disclosure relating to subfractions of NT-proBNP is provided in WO 2004/099253, the disclosure of which is hereby incorporated by reference in its entirety. According to some embodiments of the present disclosure, the NT-proBNP measured may be, or correspond to, the NT-proBNP as measured with the Elecsys® NT-proBNP assay from Roche Diagnostics, Germany.

Preanalytics with NT-proBNP are generally robust, allowing for ease in transportation of the sample to a central laboratory. For example, blood samples can be stored at room temperature for several days or may be mailed or shipped without recovery loss. In contrast, storing BNP for 48 hours at room temperature, or at 4° Celsius, has been shown to lead to a concentration loss of at least 20%.

The brain-derived natriuretic peptide family (e.g., BNP and NT-proBNP) has been investigated in the screening of certain populations for HF and findings with these markers, especially with NT-proBNP, are encouraging. Elevated values of NT-proBNP (even in asymptomatic "patients") are indicative for "heart problems." An elevated NT-proBNP indicates the presence of 'cardio-renal distress' and should prompt referral for further investigation. A low value of NT-proBNP has a relatively high negative predictive value for ruling out HF and/or left ventricular dysfunction ("LVD"), although the positive predictive value for assessing and/or diagnosis HF has been approximated at between 50-60 percent. Thus, in general, values measured for NT-proBNP may correlate to the severity of HF but neither BNP nor NT-proBNP are ideal in monitoring a patient's response to therapy.

BNP is produced predominantly (albeit not exclusively) in the ventricle and is released upon increase of wall tension. Thus, an increase of released BNP reflects predominantly dysfunctions of the ventricle or dysfunctions which originate in the atria but affect the ventricle, for example by impaired inflow or blood volume overload. In contrast to BNP, ANP is produced and released predominantly from the atrium. The level of ANP may therefore predominantly reflect atrial function.

ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min.

Therefore, depending on the time-course or properties of interest, either measurement of the active or the inactive forms of the natriuretic peptide can be advantageous.

According to an embodiment of the present disclosure, in an assessment of an individual at risk for HF the value measured for mimecan may be combined with the value for NT-proANP and/or NT-proBNP. For example, in such an embodiment, the value for NT-proBNP may be combined with the value for mimecan. Similar considerations apply for selecting an appropriate therapy, judging the risk of disease progression, and to monitoring the course of disease.

Likewise, in embodiments in which mimecan is used in assessing a patient's response to therapy, its measurement may be is combined with the measurement of ANP or BNP. Also, in embodiments in which mimecan is used to differentiate between acute and chronic HF, an exemplary marker combination comprises mimecan, ANP or proANP, and BNP or proBNP.

Cardiac Troponin Marker.

The term cardiac troponin relates to the cardiac isoforms of troponin I and troponin T. As already indicated above the term marker also relates to variants of the marker molecule, such as physiologically occurring fragments or complexes.

Troponin T has a molecular weight of about 37.000 Da. The troponin T isoform that is found in cardiac tissue (cTnT) is sufficiently divergent from skeletal muscle TnT to allow for the production of antibodies that distinguish both these TnT isoforms. TnT is considered a marker of acute myocardial damage.

Troponin I (TnI) is a 25 kDa inhibitory element of the troponin complex, found in muscle tissue. TnI binds to actin in the absence of $Ca^{2+}$, inhibiting the ATPase activity of actomyosin. The TnI isoform that is found in cardiac tissue (cTnI) is 40% divergent from skeletal muscle TnI, allowing both isoforms to be immunologically distinguished. The normal plasma concentration of cTnI is <0.1 ng/ml (4 pM). cTnI is released into the bloodstream following cardiac cell death; thus, the plasma cTnI concentration is elevated in patients with acute myocardial.

The unique cardiac isoforms of troponin I and T allow them to be distinguished immunologically from the other troponins of skeletal muscle. Therefore, the release into the blood of troponin I and T from damaged heart muscle can be specifically related to damage of cardiac tissue. Additionally, cardiac troponins may be detected from the circulation either in their free form or as a part of a complex.

According to embodiments of the instant disclosure, in the assessment of an individual at risk for HF as well as in the assessment of a patient suffering from HF, the value measured for mimecan may be combined with the value for cardiac isoform of troponin T and/or troponin I. An exemplary embodiment includes a combination of cardiac troponin T and the marker mimecan.

Marker of Inflammation.

The skilled artisan is familiar with the term marker of inflammation. Preferred markers of inflammation are interleukin-6, C-reactive protein, serum amyloid A and a S100 protein.

Interleukin-6 (IL-6) is a 21 kDa secreted protein that has numerous biological activities that can be divided into those involved in hematopoiesis and into those involved in the activation of the innate immune response. IL-6 is an acute-phase reactant and stimulates the synthesis of a variety of proteins, including adhesion molecules. Its major function is to mediate the acute phase production of hepatic proteins, and its synthesis is induced by the cytokines IL-1 and TNF-α. IL-6 is normally produced by macrophages and T lymphocytes. The normal serum concentration of IL-6 is <5 pg/ml.

C-reactive protein (CRP) is a homopentameric $Ca^{2+}$-binding acute phase protein with 21 kDa subunits that is involved in host defense. CRP synthesis is induced by IL-6, and indirectly by IL-1, since IL-1 can trigger the synthesis of IL-6 by Kupffer cells in the hepatic sinusoids. The normal plasma concentration of CRP is <3 µg/ml (30 nM) in 90% of the healthy population, and <10 µg/ml (100 nM) in 99% of healthy individuals. Plasma CRP concentrations can, e.g., be measured by ELISA. It is predominantly synthesized by the liver in response to IL-1, IL-6 or TNF-α stimulation and is involved in the regulation of the T-cell dependent immune response. Upon acute events the concentration of SAA increases up to 1000-fold reaching one milligram per milliliter. It is used to monitor inflammation in diseases as diverse as cystic fibrosis, renal graft rejection, trauma or infections. In rheumatoid arthritis it has, in certain cases, been used as a substitute for CRP, but, SAA is not yet as widely accepted.

S100-proteins form a constantly increasing family of $Ca^{2+}$-binding proteins that today includes more than 20 members. The physiologically relevant structure of S100-proteins is a homodimer but some can also form heterodimers with each other, e.g., S100A8 and S100A9. The intracellular functions range from regulation of protein phosphorylation, of enzyme activities, or of the dynamics of the cytoskeleton to involvement in cell proliferation and differentiation. As some S100-proteins are also released from cells, extracellular functions have been described as well, e.g., neuronal survival, astrocyte proliferation, induction of apoptosis and regulation of inflammatory processes. S100A8, S100A9, the heterodimer S100A8/A9 and S100A12 have been found in inflammation with S100A8 responding to chronic inflammation, while S100A9, S100A8/A9 and S100A12 are increased in acute inflammation. S100A8, S100A9, S100A8/A9 and S100A12 have been linked to different diseases with inflammatory components including some cancers, renal allograft rejection, colitis and RA. S100 markers for assessing an individual at risk for HF, or a patient having HF, for use in a marker combination according to the present disclosure include S100A8, S100A9, S100A8/A9 heterodimer, and S100A12.

sE-selectin (soluble endothelial leukocyte adhesion molecule-1, ELAM-1) is a 115 kDa, type-I transmembrane glycoprotein expressed only on endothelial cells and only after activation by inflammatory cytokines (IL-1β, TNF-α) or endotoxin. Cell-surface E-selectin is a mediator of the rolling attachment of leucocytes to the endothelium, an essential step in extravasion of leucocytes at the site of inflammation, thereby playing an important role in localized inflammatory response. Soluble E-selectin is found in the blood of healthy individuals, probably arising from proteolytic cleavage of the surface-expressed molecule. Elevated levels of sE-selectin in serum have been reported in a variety of pathological conditions.

An embodiment of the present disclosure relates to the use of mimecan as a marker molecule for HF in combination with one or more marker molecule(s) for HF in the assessment of HF from a liquid sample obtained from an individual.

As indicated above, in a method according to the present disclosure the value measured for mimecan is at least combined with the value of at least one further marker selected from the group consisting of a natriuretic peptide marker, a cardiac troponin marker, and a marker of inflammation.

One embodiment of the present disclosure relates to the use of a marker combination comprising mimecan and one or more other markers of HF selected from the group consisting of a natriuretic peptide marker, a cardiac troponin marker, and a marker of inflammation in the assessment of HF.

According to an embodiment of the present disclosure the use of the marker combination mimecan and NT-proBNP in the assessment of HF is providing.

Another embodiment of the present disclosure relates to the use of the marker combination mimecan and troponin T in the assessment of HF.

Another embodiment of the present disclosure relates to the use of the marker combination mimecan and CRP in the assessment of HF.

A further embodiment of the present disclosure relates to a marker combination comprising the markers mimecan, troponin T, NT-proBNP and CRP.

A yet even further embodiment of the present disclosure relates to a marker panel used in a method for assessing HF in vitro by biochemical markers, comprising measuring in a sample the concentration of mimecan and of one or more other marker of HF and using the concentrations determined in the assessment of HF.

A marker panel according to the present disclosure may be measured using a protein array technique, for example. An array is a collection of addressable individual markers. Such markers can be spacially addressable, such as arrays contained within microtiter plates or printed on planar surfaces where each marker is present at distinct X and Y coordinates. Alternatively, markers can be addressable based on tags, beads, nanoparticles, or physical properties. Exemplary microarrays may be prepared according to methods known in the art, such as described in U.S. Pat. No. 5,807,522, the disclosure of which is hereby incorporated by reference in its entirety. Array as used herein refers to any immunological assay with multiple addressable markers. In one embodiment the addressable markers may be antigens, whereas in another embodiment the addressable elements may be autoantibodies. A microarray is a miniaturized form of an array. Antigen as used herein refers to any molecule that can bind specifically to an antibody. The term autoantibody comprises the meaning as is as well known in the art.

An embodiment of the present disclosure relates to a protein array comprising the marker mimecan and optionally one or more other marker of HF.

An embodiment of the present disclosure relates to a protein array comprising the markers mimecan and NT-proBNP.

An embodiment of the present disclosure relates to a protein array comprising the markers mimecan and troponin T.

An embodiment of the present disclosure relates to a protein array comprising the markers mimecan and CRP.

A further embodiment of the present disclosure relates to a protein array comprising the markers mimecan, troponin T, NT-proBNP and CRP.

A yet further embodiment of the present disclosure relates to a kit comprising the reagents required to specifically measure mimecan. Also, embodiments of the present disclosure include a kit comprising the reagents required to specifically measure mimecan and the reagents required to measure the one or more other marker of HF that are used together in an HF marker combination.

In one embodiment, the present disclosure relates to a kit comprising the reagents required to specifically measure mimecan and optionally one or more other marker of HF selected from the group consisting of a natriuretic peptide marker, a cardiac troponin marker, and a marker of inflammation.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Example 1. Mouse Models of Heart Failure 1.1 The R9C Mouse Model.

It has been reported that an inherited human dilated cardiomyopathy resulted from the conversion of Arg9 to Cys in the human phospholamban (PLN) gene (PLN-R9C) (Schmitt, J. P., et al., Science 299 (2003) 1410-1413). The onset of dilated cardiomyopathy in affected patients typically commenced during adolescence, followed by progressive deterioration in cardiac function leading to crisis and mortality. A transgenic mouse model of this mutation showed similar cardiac phenotype as the affected patients and presented with dilated cardiomyopathy, decreased cardiac contractility, and premature death (Schmitt et al., 2003, supra).

The instant examples established a survival curve for the transgenic mice. As shown in FIG. 1A, the PLN-R9C mice had a median survival of only ~20 weeks with fewer than 15% persisting past 24 weeks. The first recorded deaths in the PLN-R9C line are observed at 12 weeks of age, while only one wild-type control mouse died over the 24 week period. Eight weeks is selected as a representative time point of 'early' stage disease prior to the first recorded mortality, while 16 weeks is chosen as it is the midpoint between 8 and 24 weeks (classic DCM). A detailed analysis of the pathology of isolated hearts shows evidence of ventricle and atria enlargement even at 8 weeks of age in the PLN-R9C mice. Cross-sections of isolated cardiac muscle (obtained from wild-type and PLN-R9C mice followed by hematoxylin and eosin staining also shows evidence of left ventricular dilatation, or thinning of the ventricular wall, in the transgenic animals beginning at 8 weeks, with continued progression of dilatation with age.

With reference to Table 1 (below), functional cardiac measurements are summarized based on echocardiography on the 8, 16 and 24 week old male mice. Echocardiography measurements of the thickness of the anterior and posterior wall show that the R9C mice have significant dilatation at 8 weeks, which continues to deteriorate throughout the lifespan of the mice. With reference to FIG. 1B, contractility, as assessed by cardiac shortening, is also slightly (but significantly) reduced at 8 weeks, while a more pronounced decrease is evident by 16 weeks. Female mice analyzed show identical findings as the males (data not shown).

TABLE 1

Echocardiographic and hemodynamic parameters in wildtype and R9C mice at 8, 16, and 24 weeks in male mice.

|  | WT | R9C | WT | R9C | WT | R9C |
|---|---|---|---|---|---|---|
| Age | 8 wks | 8 wks | 16 wks | 16 wks | 24 wks | 24 wks |
| Gender | M | M | M | M | M | M |
| HR (bpm) | 560 ± 6 | 567 ± 5 | 569 ± 5 | 552 ± 15 | 565 ± 9 | 502 ± 15* |
| AW (mm) | 0.66 ± 0.01 | 0.60 ± 0.01* | 0.70 ± 0.01 | 0.58 ± 0.01* | 0.71 ± 0.01 | 0.57 ± 0.01* |
| PW (mm) | 0.66 ± 0.01 | 0.61 ± 0.01* | 0.70 ± 0.01 | 0.59 ± 0.01* | 0.71 ± 0.01 | 0.57 ± 0.01* |
| LVEDD (mm) | 3.82 ± 0.05 | 4.01 ± 0.03* | 3.92 ± 0.07 | 5.01 ± 0.06* | 3.99 ± 0.05 | 5.48 ± 0.08* |
| LVESD (mm) | 1.82 ± 0.05 | 2.13 ± 0.04* | 1.84 ± 0.06 | 3.36 ± 0.09* | 1.89 ± 0.03 | 4.23 ± 0.09* |
| FS (%) | 52.7 ± 0.9 | 47.6 ± 1.2* | 53.1 ± 0.7 | 32.9 ± 1.9* | 52.9 ± 1.5 | 22.6 ± 2.1* |
| VCFc (circ/s) | 10.5 ± 0.2 | 9.1 ± 0.2* | 10.5 ± 0.1 | 7.0 ± 0.5* | 10.9 ± 0.3 | 5.1 ± 0.5* |

TABLE 1-continued

Echocardiographic and hemodynamic parameters in wildtype and
R9C mice at 8, 16, and 24 weeks in male mice.

|  | WT | R9C | WT | R9C | WT | R9C |
|---|---|---|---|---|---|---|
| PAVc (cm/s) | 102.4 ± 2.4 | 97.8 ± 2.6 | 110.1 ± 3.7 | 85.3 ± 3.2* | 111.3 ± 2.9 | 73.6 ± 3.1* |
| AVA (m/s2) | 65.7 ± 1.3 | 60.6 ± 1.6 | 66 ± 3.2 | 47.9 ± 2.5* | 67.1 ± 3.1 | 40 ± 2.2* |
| Samples (n) | 6 | 9 | 6 | 9 | 5 | 5 |

Values in Table 1 are mean ± SEM.
Symbols used in Table 1:
HR = Heart Rate;
AW, PW = Anterior and Posterior Wall Thickness (Left Ventricle);
LVEDD, LVESD = Left Ventricular End Diastolic and Systolic Dimension, respectively;
FS = Fractional Shortening = (LVEDD − LVESD)/LVEDD × 100%;
ETC = Ejection Time corrected for HR;
VCFC = Velocity of Circumferential Shortening corrected for HR = FS/ETC;
PAVC = Peak Aortic Velocity corrected for HR;
E-wave = Early-filling transmitral diastolic wave;
LVESP, LVEDP = Left Ventricular End Systolic and Diastolic Pressure;
+dP/dtmax = Maximum positive 1st derivative of the left ventricular pressure;
−dP/dtmax = Maximum negative 1st derivative of the left ventricular pressure;
AVA = aortic velocity acceleration (PAVc/Acceleration Time);
*P < 0.05 compared with WT.

1.2 The Aortic Banding (AB) Mouse Model.

In this mouse model pressure-overload caused by aortic banding (AB) induces cardiac-hypertrophy and heart failure.

By surgical intervention pressure-overload is performed in C57BL mice. The coarction of the ascending aorta (known as aortic banding) induces cardiac hypertrophy and growth of the myocardial muscle, especially in the left ventricle as a primary response to coarction of the aorta. In the later stages of this mouse model the heart becomes hypertrophic and finally dilated. This model is well characterized and has proven to be highly reproducible with a low mortality rate of 10-15% or less based on experience. After coarction this animal model allows for evaluating the progress of development of left ventricular hypertrophy and heart failure in response to hemodynamic stress.

Briefly C57BL mice are anesthetized with mixed Ketamine (90 mg/kg) and Rompun (10 mg/Kg) and the aorta is ligated using 25-gauge needle. Sham operated mice undergo the same surgical procedure, except that the ligation is not tightened against the needle.

Experimental Time Points.

To examine the hypertrophic response, banded animals and sham-operated controls are sacrificed at one, two, four, and eight weeks post intervention. Cardiac function and the development of hypertrophy are assessed by echocardiographic analysis and confirmed post mortem by examining the histology. Table 2 shows an overview over the cardiac function evaluated at the various time points by echocardiography. General information relating to the echocardiographic parameters given in Table 2 are known in the art and such general information may be found in Asahi, M., et al., Proc. Natl. Acad. Sci. USA 101 (2004) 9199-9204, and Oudit, G. Y., et al., Nat. Med. 9 (2003) 1187-1194, which is hereby incorporated by reference.

TABLE 2

| Parameter | 2 wk sham | 2 wk AB | 4 wk sham | 4 wk AB | 8 wk sham | 8 wk AB |
|---|---|---|---|---|---|---|
| Heart rate (bpm) | 271.6 ± 31.2 | 286.3 ± 39.1 | 275.3 ± 25.8 | 276.5 ± 28.1 | 255.5 ± 23.9 | 310.8 ± 18.0 |
| Maximum Volume (uL) | 32.2 ± 2.3 | 36.4 ± 3.4 | 36.9 ± 1.1 | 40.8 ± 1.6 | 38.1 ± 1.5 | 48.9 ± 4.4 |
| Minimum Volume (uL) | 13.7 ± 2.4 | 15.8 ± 3.3 | 14.7 ± 1.9 | 25.7 ± 0.9 | 18.4 ± 0.5 | 36.5 ± 3.7 |
| End-systolic Volume (uL) | 14.7 ± 2.8 | 16.9 ± 3.3 | 15.5 ± 2.1 | 28.0 ± 0.7 | 19.3 ± 0.5 | 40.2 ± 4.3 |
| End-diastolic Volume (uL) | 30.6 ± 2.4 | 34.5 ± 3.2 | 35.2 ± 1.1 | 39.8 ± 1.6 | 36.8 ± 1.4 | 47.2 ± 4.1 |
| Maximum Pressure (mmHg) | 93.1 ± 3.5 | 149.2 ± 4.8 | 92.6 ± 0.8 | 153.5 ± 6.1 | 93.6 ± 5.0 | 169.8 ± 10.2 |
| Minimum Pressure (mmHg) | 4.9 ± 1.3 | 3.2 ± 0.4 | 3.6 ± 0.1 | 7.3 ± 3.6 | 4.1 ± 0.5 | 6.2 ± 1.9 |
| End-systolic Pressure (mmHg) | 87.3 ± 4.3 | 139.4 ± 2.8 | 89.2 ± 1.0 | 149.6 ± 5.0 | 90.5 ± 4.9 | 168.3 ± 9.8 |
| End-diastolic Pressure (mmHg) | 14.0 ± 3.2 | 10.6 ± 2.7 | 13.0 ± 0.7 | 16.8 ± 4.8 | 16.5 ± 1.4 | 16.9 ± 3.1 |
| Stroke Volume (uL) | 18.6 ± 1.0 | 20.6 ± 0.7 | 22.2 ± 2.3 | 15.1 ± 1.2 | 19.7 ± 1.4 | 12.4 ± 1.0 |
| Ejection Fraction (%) | 58.7 ± 5.1 | 57.9 ± 4.5 | 60.0 ± 5.3 | 36.8 ± 1.9 | 51.5 ± 1.6 | 25.8 ± 2.0 |
| Cardiac Output (uL/min) | 5113.5 ± 819.2 | 5879.1 ± 714.0 | 6114.8 ± 897.0 | 4108.6 ± 310.3 | 5066.0 ± 653.3 | 3893.8 ± 466.1 |
| Stroke Work (mmHg * uL) | 1339.6 ± 134.0 | 2196.3 ± 94.6 | 1577.8 ± 134.4 | 1477.8 ± 99.6 | 1451.8 ± 130.4 | 1179.2 ± 104.1 |
| Arterial Elastance (Ea) (mmHg/uL) | 4.8 ± 0.4 | 6.8 ± 0.3 | 4.1 ± 0.4 | 10.1 ± 0.7 | 4.7 ± 0.4 | 14.1 ± 1.7 |
| dPdt max (mmHg/sec) | 5481.6 ± 491.1 | 6785.3 ± 434.2 | 6036.0 ± 352.9 | 5133.2 ± 621.4 | 5755.8 ± 652.9 | 6454.4 ± 712.0 |
| dPdt min (mmHg/sec) | −5049.6 ± 426.9 | −7427.5 ± 685.3 | −4743.3 ± 287.7 | −5484.75 ± 412.2 | −4564.5 ± 525.8 | −7625 ± 586.5 |
| dVdt max (uL/sec) | 883.0 ± 61.2 | 758.0 ± 29.8 | 856.5 ± 27.4 | 1152.8 ± 206.3 | 1188.0 ± 114.1 | 1041.2 ± 109.6 |
| dVdt min (uL/sec) | −679.6 ± 71.4 | −696.3 ± 30.6 | −703.5 ± 52.2 | −921.0 ± 158.0 | −1000.5 ± 76.8 | −938.4 ± 126.2 |
| P@dVdt max (mmHg) | 9.0 ± 2.5 | 7.4 ± 2.6 | 4.6 ± 0.4 | 10.3 ± 3.4 | 6.2 ± 1.0 | 13.3 ± 4.5 |
| P@dPdt max (mmHg) | 44.1 ± 2.1 | 46.3 ± 3.5 | 49.0 ± 2.6 | 47.1 ± 2.8 | 49.6 ± 5.6 | 52.8 ± 3.6 |
| V@dPdt max (uL) | 31.2 ± 2.4 | 35.5 ± 3.5 | 35.0 ± 1.1 | 39.7 ± 1.6 | 37.0 ± 1.5 | 47.3 ± 4.4 |
| V@dPdt min (uL) | 14.7 ± 2.6 | 17.1 ± 3.2 | 15.6 ± 1.9 | 27.0 ± 0.7 | 19.2 ± 0.4 | 39.0 ± 4.3 |
| Tau_w (msec) | 11.4 ± 1.2 | 8.6 ± 0.7 | 10.7 ± 0.9 | 11.2 ± 1.3 | 11.3 ± 0.5 | 8.8 ± 0.4 |
| Tau_g (msec) | 15.8 ± 1.5 | 12.1 ± 1.2 | 17.5 ± 0.7 | 17.4 ± 1.0 | 17.5 ± 1.0 | 15.6 ± 1.0 |
| Maximal Power (mWatts) | 6.4 ± 0.6 | 9.5 ± 0.4 | 6.8 ± 0.5 | 8.8 ± 0.5 | 7.3 ± 0.7 | 9.0 ± 0.5 |
| Preload adjusted maximal power (mWattsuL^2) | 74.8 ± 16.5 | 85.0 ± 12.9 | 55.5 ± 2.4 | 57.3 ± 7.4 | 53.6 ± 3.0 | 46.1 ± 11.5 |

In addition to functional parameters histology by Hematoxylin/Eosin (HE) staining is performed on cardiac tissue from AB mice and control mice at 2, 4, and 8 weeks. Histology confirms the expected necrotic and remodeling processes for the AB mice, whereas heart tissue in sham operated mice does not show any significant changes. At two weeks after surgery the ventricle of a ligated mouse shows significant left ventricular hypertrophy which after four weeks has further progressed and at eight weeks post-surgery closely resembles end stage dilated cardiomyopathy.

Example 2. Microarray Analysis

Sample Preparation and Mass Spectroscopy.

Crude tissue preparations are used for microarray analysis without further isolation of organelles. The microarray data analysis methodology is further described in the above incorporated U.S. Pat. No. 5,807,522, and other references known in the art.

Heart Homogenization and Organelle Isolation.

Hearts are isolated, atria removed, the ventricles carefully minced with a razor blade and rinsed extensively with ice-cold PBS (phosphate buffered saline) to remove excess blood. Tissue is homogenized for 30 seconds (s) using a loose fitting hand-held glass homogenizer in 10 ml lysis buffer (250 mM sucrose, 50 mM Tris-HCl pH 7.6, 1 mM MgCl2, 1 mM DDT (dithiothreitol), and 1 mM PMSF (phenylmethylsulphonyl fluoride). All subsequent steps are performed at 4° C. The lysate is centrifuged in a benchtop centrifuge at 800×g for 15 min; the supernatant serves as a source for cytosol, mitochondria, and microsomal fractions. The pellet containing nuclei is diluted in 8 ml of lysis buffer and layered onto 4 ml of 0.9 M sucrose buffer (0.9 M sucrose, 50 mM Tris-HCl pH 7.6, 1 mM MgCl2, 1 mM DDT, and 1 mM PMSF) and centrifuged at 1000×g for 20 min at 4° C. The resulting pellet is resuspended in 8 ml of a 2 M sucrose buffer (2 M sucrose, 50 mM Tris-HCl pH 7.4, 5 mM MgCl2, 1 mM DTT, and 1 mM PMSF), layered onto 4 ml of 2 M sucrose buffer and pelleted by ultracentrifugation at 150,000×g for 1 h (Beckman SW40.1 rotor). The nuclei are recovered as a pellet. The mitochondria are isolated from the supernatant by re-centrifugation at 7500×g for 20 min at 4° C.; the resulting pellet is washed twice in lysis buffer. Microsomes are pelleted by ultracentrifugation of the post-mitochondrial cytoplasm at 100,000×g for 1 h in a Beckman SW41 rotor. The supernatant served as the cytosolic fraction (=cyto).

Organelle Extraction.

Soluble mitochondrial proteins are extracted by incubating the mitochondria in hypotonic lysis buffer (10 mM HEPES, pH 7.9, 1 mM DTT, 1 mM PMSF), for 30 min on ice. The suspension is sonicated briefly and debris removed by centrifugation at 13,000×g for 30 min. The supernatant serves as the "mito 1" fraction. The resulting insoluble pellet is resuspended in membrane detergent extraction buffer (20 mM Tris-HCl, pH 7.8, 0.4 M NaCl, 15% glycerol, 1 mM DTT, 1 mM PMSF, 1.5% Triton-X-100) and shaken gently for 30 min followed by centrifugation at 13,000×g for 30 min; the supernatant served as "mito 2" fraction.

Membrane-associated proteins are extracted by resuspending the microsomes in membrane detergent extraction buffer. The suspension is incubated with gentle shaking for 1 h and insoluble debris removed by centrifugation at 13,000×g for 30 min. The supernatant serves as the "micro" fraction.

Digestion of Organelle Extracts and MudPIT Analysis.

An aliquot of about 100 µg total protein (as determined by Bradford assay) from each fraction is precipitated overnight with 5 vol of ice-cold acetone at about 20° C., followed by centrifugation at 13,000×g for 15 min. The protein pellet is solubilized in a small volume of 8 M urea, 50 mM Tris-HCl, pH 8.5, 1 mM DTT, for 1 h at 37° C., followed by carboxyamidomethylation with 5 mM iodoacetamide for 1 h at 37° C. in the dark. The samples are then diluted to 4 M urea with an equal vol of 100 mM ammonium bicarbonate, pH 8.5, and digested with a 1:150-fold ratio of endoproteinase Lys-C (Roche Diagnostics, Laval, Quebec, Canada) at 37° C. overnight. The next day, the samples are diluted to 2 M urea with an equal vol of 50 mM ammonium bicarbonate pH 8.5, supplemented with CaCl2 to a final concentration of 1 mM, and incubated overnight with Poroszyme trypsin beads (Applied Biosystems, Streetsville, Ontario, Canada) at 30° C. with rotation. The resulting peptide mixtures are solid phase-extracted with SPEC-Plus PT C18 cartridges (Ansys Diagnostics, Lake Forest, Calif.) according to the instructions of the manufacturer and stored at −80° C. until further use. A fully-automated 20 hour (h) long 12-step multi-cycle MudPIT procedure is set up as described (Kislinger, T., et al., Mol. Cell Proteom. 2 (2003) 96-106). Briefly, an HPLC quaternary pump is interfaced with an LCQ DECA XP ion trap mass spectrometer (Thermo Finnigan, San Jose, Calif.). A 100-µm i.d. fused silica capillary microcolumn (Polymicro Technologies, Phoenix, Ariz.) is pulled to a fine tip using a P-2000 laser puller (Sutter Instruments, Novato, Calif.) and packed with 8 cm of 5 µm Zorbax Eclipse XDB-C18 resin (Agilent Technologies, Mississauga, Ontario, Canada), followed by 6 cm of 5 µm Partisphere strong cation exchange resin (Whatman, Clifton, N.J.). Individual samples are loaded manually onto separate columns using a pressure vessel. Chromatography solvent conditions are exactly as described in Kislinger, T., et al., Mol. Cell Proteom. 2 (2003) 96-106.

Protein Identification and Validation.

The SEQUEST database search algorithm is used to match peptide tandem mass spectra to peptide sequences in a locally-maintained minimally redundant FASTA formatted database populated with mouse and human protein sequences obtained from the Swiss-Prot/TrEMBL and IPI databases. To statistically assess the empirical False-Discovery Rate to control for, and hence, minimize false positive identifications, all of the spectra are searched against protein sequences in both the normal (Forward) and inverted (Reverse) amino acid orientations (Kislinger, T., et al., Mol. Cell Proteom. 2 (2003) 96-106). The STATQUEST filtering algorithm is then applied to all putative search results to obtain a measure of the statistical reliability (confidence score) for each candidate identification (cutoff p-value 5, corresponding to an 85% or greater likelihood of being a correct match). High-confidence matches are parsed into an in-house SQL-type database using a Perl-based script. The database is designed to accommodate database search results and spectral information (scan headers) for multiple peptides matching to a given protein, together with information regarding the sample name, experiment number, MudPIT step, organelle source, amino acid sequence, molecular mass, isoelectric point, charge, and confidence level. Only those proteins with a predicted confidence p value of 95% or more, and for which at least two spectra are collectively detected, are retained for further analysis.

Example 3. Statistical Evaluation of the Data Obtained in the Model Systems 3.1 Statistical Methods Used to Generate P-Values of Differential Expression for the R9C Mouse Model.

The raw data obtained with the methods as described in Example 2 consists of 6190 proteins each with spectral counts, the sum of all spectra associated with the protein, for each of the 137 different experimental runs. The raw data, 6190 subset of proteins, is subjected to global normalization which first separates the data within each run into an equal number of groups, set at 100 for our analysis, based on their spectral counts. LOESS (Cleveland, W. S. and Devlin, S. J., Journal of the American Statistical Association 83 (1988) 596-610) is then performed on each group (1-100) adjusting for differences in spectral counts across a set of genes with similar spectral counts.

Based on our raw data we constructed two linear models, the first model uses control/disease, time (8W, 16W, end) and location (cyto, micro, mitol, mitoll) as factors and is described using:

$$\text{run count} = \beta 0 + \beta 1 \text{time} + \beta 2 \text{time}^2 + \beta 3 \text{location} + \beta 4 \text{control} \quad (1).$$

The second model uses only time (8W, 16W, end) and location (cyto, micro, mitol, mitoll) as factors and is described using:

$$\text{run count} = \beta 0 + \beta 1 \text{time} + \beta 2 \text{time}^2 + \beta 3 \text{location} \quad (2),$$

where β0 is the intercept term and β1, β2, β3, and β4 are the slope estimates for the variables time, time squared, location, and control/disease.

The two models are compared using Anova, with the null hypothesis being that there is no difference between the two models. A low p-value then indicates that there is not enough proof to say the two models are the same. The extra information indicates the state (i.e., control/disease) appears to be a significant component of the model. In order to extract proteins that have a significant change in relative protein abundance between our control and disease models our list of 6190 proteins is ranked based on their computed p-values. This generates a set of 593 proteins with p-values <0.05.

In order to account for multiple hypothesis testing from the above model the p-values are then corrected using false discovery rate (FDR) correction, specifically Benjamini-Hochberg FDR correction (Benjamini, Y., and Hochberg, Y., Journal of the Royal Statistical Society B. 57 (1995) 289-300). This generates a set of 40 proteins with corrected p-values <0.05 for the R9C mouse model.

3.2 Statistical Methods Used to Generate P-Values of Differential Expression for the Aortic Banding Mouse Model.

From 68 experimental runs in the aortic banding mouse model 3152 proteins with spectral counts are identified. The same data analysis is applied to the datasets for the aortic banding mouse model as described above for the R9C mouse model.

Example 4

4.1. ELISA for the Measurement of Mimecan in Human Serum and Plasma Samples.

For detection of mimecan in human serum or plasma, a sandwich ELISA is developed. For capture and detection of the antigen, aliquots of an anti-mimecan polyclonal antibody from R&D Systems (Catalogue number: AF 2660) are conjugated with biotin and digoxigenin, respectively.

Streptavidin-coated 96-well microtiter plates are incubated with 100 μl biotinylated anti-mimecan polyclonal antibody for 60 min at 0.2 μg/ml in 1×PBS solution. After incubation, plates are washed three times with 1×PBS+0.02% Tween-20, blocked with PBS+2% BSA (bovine serum albumen) for 45 min and then washed again three times with 1×PBS+0.02% Tween-20. Wells are then incubated for 1 h with 100 μl of either a serial dilution of the recombinant mimecan as standard antigen or with diluted serum or plasma samples (1:5 in 1×PBS+1% BSA) from patients or control individuals, respectively. After binding of mimecan, plates are washed three times with 1×PBS+0.02% Tween-20. For specific detection of bound mimecan, wells are incubated with 100 μl of digoxigenylated anti-mimecan polyclonal antibody for 45 min at 0.2 μg/ml in 1×PBS+1% BSA. Thereafter, plates are washed three times to remove unbound antibody. In a next step, wells are incubated with 100 μl of 75 mU/ml anti-digoxigenin-POD conjugates (Roche Diagnostics GmbH, Mannheim, Germany, Catalog No. 1633716) for 30 min in 1×PBS+1% BSA. Plates are subsequently washed six times with the same washing buffer as above. For detection of antigen-antibody complexes, wells are incubated with 100 μl ABTS solution (Roche Diagnostics GmbH, Mannheim, Germany, Catalog No. 11685767) and the optical density (OD) is measured after 15 min at 405 and 492 nm with an ELISA reader.

4.2. Mimecan ELISA with Sera of Patients Having HF and Obtained Out of the Clinical Routine and Apparently Healthy Donors, Respectively.

In order to further evaluate the utility of the mimecan assay under routine clinical conditions a panel of sera from HF patients (n=241) and from apparently healthy control patients (n=146) is investigated. As mentioned before, sera are diluted 1:5 in 1×PBS+1% BSA. Table 3 shows the result for these extended panels:

TABLE 3

Mimecan ELISA results (panel with HF samples from clinical routine).

| HF samples Sample-Id. | Mimecan ELISA [ng/mL] | NHS samples Sample-Id. | Mimecan ELISA [ng/mL] |
|---|---|---|---|
| 4143 | 14.31 | 1 | 7.61 |
| 4144 | 28.36 | 2 | 0.95 |
| 4145 | 11.41 | 3 | 4.91 |
| 4146 | 20.76 | 4 | 10.29 |
| 4150 | 48.10 | 5 | 0.00 |
| 4151 | 32.78 | 6 | 16.90 |
| 4152 | 51.59 | 7 | 3.18 |
| 4153 | 31.65 | 8 | 3.04 |
| 4154 | 38.64 | 9 | 5.38 |
| 4155 | 26.56 | 10 | 0.00 |
| 4157 | 70.99 | 11 | 2.39 |
| 4158 | 46.94 | 12 | 6.01 |
| 4159 | 43.53 | 13 | 45.45 |
| 4161 | 33.28 | 14 | 15.42 |
| 4162 | 27.75 | 15 | 23.78 |
| 4163 | 4.77 | 16 | 4.91 |
| 4164 | 40.47 | 17 | 8.60 |
| 4170 | 85.11 | 18 | 10.97 |
| 4171 | 64.11 | 19 | 0.00 |
| 4173 | 37.36 | 20 | 22.98 |
| 4174 | 43.93 | 21 | 6.25 |
| 4175 | 19.53 | 22 | 13.34 |
| 4176 | 33.49 | 23 | 4.68 |
| 4178 | 18.03 | 24 | 1.62 |
| 4181 | 27.09 | 25 | 3.85 |
| 4182 | 33.99 | 26 | 22.18 |
| 4187 | 67.39 | 27 | 0.00 |
| 4189 | 61.88 | 28 | 2.39 |
| 4190 | 7.31 | 29 | 0.00 |

TABLE 3-continued

Mimecan ELISA results (panel with HF samples from clinical routine).

| HF samples Sample-Id. | Mimecan ELISA [ng/mL] | NHS samples Sample-Id. | Mimecan ELISA [ng/mL] |
|---|---|---|---|
| 4191 | 32.85 | 30 | 12.63 |
| 4192 | 6.54 | 31 | 14.42 |
| 4193 | 38.26 | 32 | 14.42 |
| 4194 | 21.00 | 33 | 8.35 |
| 4196 | 16.03 | 44 | 20.20 |
| 4198 | 34.93 | 45 | 8.25 |
| 4199 | 44.17 | 46 | 9.95 |
| 4200 | 19.11 | 47 | 5.47 |
| 4202 | 54.94 | 48 | 11.19 |
| 4203 | 28.02 | 49 | 12.18 |
| 4204 | 12.46 | 50 | 9.20 |
| 4205 | 37.89 | 51 | 13.57 |
| 4206 | 22.75 | 52 | 11.57 |
| 4212 | 17.02 | 53 | 7.67 |
| 4213 | 48.52 | 54 | 9.68 |
| 4588 | 28.42 | 55 | 4.47 |
| 4589 | 30.11 | 56 | 14.82 |
| 4590 | 49.04 | 57 | 12.01 |
| 4591 | 4.99 | 58 | 13.29 |
| 4594 | 14.33 | 59 | 16.03 |
| 4595 | 20.23 | 60 | 14.36 |
| 4597 | 21.59 | 61 | 12.12 |
| 4606 | 40.07 | 62 | 14.82 |
| 4607 | 36.73 | 63 | 12.84 |
| 4608 | 66.99 | 64 | 9.46 |
| 4613 | 14.15 | 65 | 10.65 |
| 4622 | 60.70 | 66 | 15.97 |
| 4623 | 45.94 | 67 | 17.44 |
| 4624 | 47.91 | 68 | 11.85 |
| 4625 | 64.02 | 69 | 13.85 |
| 4633 | 55.99 | 70 | 15.34 |
| 4640 | 49.54 | 71 | 11.74 |
| 4641 | 21.89 | 72 | 12.68 |
| 4643 | 52.86 | 73 | 25.57 |
| 4676 | 9.02 | 74 | 12.84 |
| 4677 | 70.46 | 75 | 13.52 |
| 4678 | 23.38 | 76 | 68.96 |
| 4680 | 61.66 | 77 | 54.79 |
| 4681 | 23.88 | 78 | 121.01 |
| 4684 | 35.94 | 79 | 100.57 |
| 4685 | 27.89 | 80 | 69.22 |
| 4687 | 27.68 | 81 | 104.15 |
| 4688 | 28.94 | 82 | 123.01 |
| 4690 | 0.00 | 83 | 62.39 |
| 4691 | 35.49 | 84 | 63.96 |
| 4692 | 45.69 | 85 | 70.54 |
| 4693 | 37.07 | 86 | 75.55 |
| 4694 | 15.60 | 87 | 113.07 |
| 4695 | 45.20 | 88 | 97.02 |
| 4696 | 40.54 | 89 | 84.33 |
| 4697 | 19.07 | 90 | 64.49 |
| 4698 | 16.90 | 91 | 81.66 |
| 4699 | 43.63 | 92 | 90.51 |
| 4700 | 19.26 | 93 | 136.42 |
| 4701 | 14.33 | 94 | 85.67 |
| 4702 | 55.46 | 95 | 65.80 |
| 4703 | 9.61 | 96 | 113.35 |
| 4704 | 42.79 | 97 | 73.44 |
| 4705 | 14.24 | 98 | 107.48 |
| 4706 | 48.04 | 99 | 96.74 |
| 4707 | 39.72 | 100 | 76.08 |
| 4708 | 46.18 | 101 | 104.98 |
| 4711 | 32.93 | 102 | 100.30 |
| 4712 | 16.52 | 103 | 56.36 |
| 4713 | 48.04 | 104 | 85.40 |
| 4714 | 131.71 | 105 | 79.26 |
| 4715 | 189.20 | 106 | 37.11 |
| 4717 | 168.44 | 107 | 36.68 |
| 4720 | 102.50 | 108 | 26.45 |
| 4726 | 138.80 | 109 | 32.07 |
| 4728 | 262.50 | 110 | 42.87 |
| 4729 | 117.30 | 111 | 39.52 |
| 4730 | 262.50 | 112 | 41.97 |
| 4732 | 89.97 | 113 | 35.59 |
| 4736 | 161.13 | 114 | 36.57 |
| 4737 | 172.31 | 115 | 33.55 |
| 4738 | 166.84 | 116 | 79.89 |
| 4739 | 163.03 | 117 | 43.09 |
| 4790 | 221.41 | 118 | 31.22 |
| 4795 | 156.13 | 119 | 81.28 |
| 4799 | 129.66 | 120 | 38.20 |
| 4805 | 125.89 | 121 | 25.84 |
| 4806 | 80.33 | 122 | 16.71 |
| 4807 | 82.19 | 123 | 25.63 |
| 4808 | 183.82 | 124 | 28.30 |
| 4811 | 132.30 | 125 | 24.22 |
| 4813 | 193.98 | 126 | 32.49 |
| 4815 | 136.13 | 127 | 27.27 |
| 4819 | 233.07 | 128 | 22.21 |
| 4820 | 102.50 | 129 | 31.33 |
| 4821 | 54.01 | 130 | 32.70 |
| 4822 | 175.24 | 131 | 32.92 |
| 4823 | 132.59 | 132 | 32.07 |
| 4827 | 88.62 | 133 | 42.64 |
| 4830 | 206.90 | 134 | 27.48 |
| 4831 | 207.61 | 135 | 33.34 |
| 4832 | 182.82 | 136 | 46.69 |
| 4836 | 206.19 | 137 | 41.80 |
| 4837 | 52.96 | 138 | 53.64 |
| 4838 | 262.50 | 139 | 60.42 |
| 4843 | 104.70 | 140 | 42.68 |
| 4845 | 65.28 | 141 | 67.32 |
| 4846 | 262.50 | 142 | 49.39 |
| 4847 | 108.59 | 143 | 57.63 |
| 4849 | 180.50 | 144 | 72.42 |
| 4850 | 140.59 | 145 | 51.05 |
| 4851 | 210.12 | 146 | 46.99 |
| 4853 | 118.44 | 147 | 73.86 |
| 4855 | 262.50 | 148 | 16.00 |
| 4857 | 200.21 | 149 | 56.40 |
| 4858 | 213.36 | 150 | 89.41 |
| 4860 | 137.90 | 151 | 54.10 |
| 4862 | 110.82 | 152 | 64.95 |
| 4867 | 58.46 | 153 | 54.40 |
| 4868 | 262.50 | 154 | 60.89 |
| 4869 | 14.31 | 155 | 30.98 |
| 4871 | 36.89 | 156 | 41.50 |
| 4872 | 19.34 | n | 146 |
| 4873 | 26.96 | | |
| 4876 | 96.18 | | |
| 4878 | 46.97 | | |
| 4879 | 79.62 | | |
| 4880 | 60.00 | | |
| 4881 | 54.38 | | |
| 4882 | 64.39 | | |
| 4886 | 37.44 | | |
| 4889 | 86.50 | | |
| 4893 | 18.65 | | |
| 4894 | 24.32 | | |
| 4895 | 67.86 | | |
| 4896 | 53.90 | | |
| 4900 | 61.99 | | |
| 4902 | 93.64 | | |
| 4904 | 53.42 | | |
| 4905 | 44.11 | | |
| 4906 | 33.88 | | |
| 4907 | 56.44 | | |
| 4911 | 29.86 | | |
| 4912 | 27.89 | | |
| 4913 | 52.83 | | |
| 4914 | 35.27 | | |
| 4916 | 47.78 | | |
| 4917 | 72.58 | | |
| 4928 | 44.11 | | |
| 4929 | 51.29 | | |
| 4930 | 52.47 | | |
| 4937 | 67.86 | | |
| 4940 | 36.03 | | |

TABLE 3-continued

Mimecan ELISA results (panel with HF samples from clinical routine).

| HF samples Sample-Id. | Mimecan ELISA [ng/mL] | NHS samples Sample-Id. | Mimecan ELISA [ng/mL] |
|---|---|---|---|
| 4941 | 66.57 | | |
| 4942 | 73.51 | | |
| 4943 | 26.76 | | |
| 4944 | 34.52 | | |
| 4945 | 93.34 | | |
| 4948 | 37.66 | | |
| 4949 | 47.89 | | |
| 4950 | 42.53 | | |
| 4952 | 78.38 | | |
| 4953 | 68.50 | | |
| 4954 | 86.21 | | |
| 4955 | 69.29 | | |
| 4956 | 86.50 | | |
| 4957 | 98.30 | | |
| 4961 | 15.17 | | |
| 4965 | 82.12 | | |
| 4967 | 33.02 | | |
| 4968 | 79.37 | | |
| 4971 | 46.84 | | |
| 4974 | 99.84 | | |
| 4975 | 102.74 | | |
| 4976 | 137.16 | | |
| 4977 | 42.68 | | |
| 4978 | 24.85 | | |
| 4979 | 142.83 | | |
| 4981 | 80.02 | | |
| 4982 | 89.24 | | |
| 4983 | 91.08 | | |
| 4986 | 75.64 | | |
| 4995 | 81.82 | | |
| 4996 | 156.76 | | |
| 4997 | 63.85 | | |
| 5004 | 210.31 | | |
| 5005 | 45.35 | | |
| 5008 | 64.95 | | |
| 5009 | 40.77 | | |
| 5010 | 45.20 | | |
| 5011 | 262.5 | | |
| 5012 | 141.91 | | |
| 5020 | 92.75 | | |
| 5021 | 262.5 | | |
| 5022 | 36.55 | | |
| 5023 | 105.14 | | |
| 5026 | 98.65 | | |
| 5030 | 46.69 | | |
| 5031 | 91.08 | | |
| 5034 | 65.11 | | |
| 5035 | 76.28 | | |
| 5036 | 96.79 | | |
| 5042 | 71.94 | | |
| 5043 | 92.08 | | |
| 5044 | 50.15 | | |
| 5045 | 96.28 | | |
| 5046 | 108.42 | | |
| 5048 | 81.98 | | |
| 5049 | 184.18 | | |
| 5050 | 119.77 | | |
| 5055 | 52.42 | | |
| 5056 | 95.44 | | |
| 5057 | 92.42 | | |
| 5058 | 64.01 | | |
| 5063 | 107.03 | | |
| 5064 | 60.57 | | |
| 5065 | 129.75 | | |
| n | 241 | | |

The data summarized in Table 3 have also been used to calculate the box blots box-plots shown in FIG. 3. FIG. 3 demonstrates that there is quite a difference in the average mimecan values as measured in sera derived from patients with heart failure as compared to mimecan values as measured in sera derived from apparently healthy control individuals. An increased value for mimecan is indicative of heart failure.

Example 5. Example 5.1

The Marker Combination NT-proBNP and Mimecan

The marker combination NT-proBNP and mimecan is evaluated for the differentiation of patients in stage B and stages C plus D, respectively. Diagnostic accuracy is assessed by analyzing individual liquid samples obtained from well-characterized groups of individuals, i.e., 50 individuals in stage B according to the ACA/ACC criteria for classification of HF and 50 patients suffering from HF and having stage C according to the ACA/ACC criteria for classification of HF. NT-proBNP as measured by a commercially available assay (Roche Diagnostics, NT-proBNP-assay (Cat. No. 03 121 640 160 for Elecsys® Systems immunoassay analyzer) and mimecan measured as described above are quantified in a serum sample obtained from each of these individuals. ROC-analysis is performed according to Zweig, M. H., and Campbell, G., supra. Discriminatory power for differentiating patients in stage C from individuals in stage B for the combination of mimecan with the established marker NT-proBNP is calculated by regularized discriminant analysis (Friedman, J. H., Regularized Discriminant Analysis, Journal of the American Statistical Association 84 (1989) 165-175).

Example 5.2. The Marker Combination Troponin T and Mimecan

The marker combination troponin T and mimecan is evaluated for the differentiation of patients suffering from an acute cardiac event from patients suffering from chronic heart disease, respectively. Diagnostic accuracy is assessed by analyzing individual liquid samples obtained from well-characterized groups of individuals, i.e., 50 individuals diagnosed as having an acute cardiac event and 50 individuals diagnosed as having chronic cardiac disease. Troponin T as measured by a commercially available assay (Roche Diagnostics, troponin T-assay (Cat. No. 201 76 44 for Elecsys® Systems immunoassay analyzer) and mimecan measured as described above are quantified in a serum sample obtained from each of these individuals. ROC-analysis is performed according to Zweig, M. H., and Campbell, G., supra. Discriminatory power for differentiating patients in stage C from individuals in stage B for the combination of mimecan with the established marker troponin T is calculated by regularized discriminant analysis (Friedman, J. H., J. of the American Statistical Association 84 (1989) 165-175).

Example 5.3. The Marker Combination Mimecan and CRP

The marker combination C-reactive protein (CRP) and mimecan is evaluated for the differentiation of patients diagnosed as having a cardiomyopathy versus controls not suffering from any confounding heart disease, respectively. Diagnostic accuracy is assessed by analyzing individual liquid samples obtained from well-characterized groups of 50 individuals with cardiomyopathy and of 50 healthy control individuals. CRP as measured by a commercially available assay (Roche Diagnostics, CRP-assay (Tina-quant C-reactive protein (latex) high sensitive assay—Roche Cat. No. 11972855 216) and mimecan measured as described above are quantified in a serum sample obtained from each of these individuals. ROC-analysis is performed according to Zweig, M. H., and Campbell, G., supra. Discriminatory power for differentiating patients in stage C from individuals in stage B for the combination of mimecan with the established marker CRP is calculated by regularized discriminant analysis (Friedman, J. H., J. of the American Statistical Association 84 (1989) 165-175).

All publications, patents and applications are herein incorporated by reference in their entirety to the same extent as if each such reference was specifically and individually indicated to be incorporated by reference in its entirety.

While this disclosure has been described, for the purposes of clarity and understanding, as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of diagnosing heart failure in an individual suspected of having heart failure, the method comprising the steps of:
   contacting, in-vitro, a portion of a sample from the individual with an antibody or fragment thereof having specific binding affinity for a marker mimecan having an amino acid sequence at least 90% identical to SEQ ID NO: 1, thereby forming a complex between the antibody or fragment thereof and the marker mimecan present in the sample, the antibody having a detectable label, the sample comprising one of serum, plasma and whole blood;
   separating the complex formed in said step of contacting from antibody or fragment thereof not comprising the complex;
   quantifying a signal from the detectable label of the antibody or fragment thereof comprising the complex formed in said step of contacting, the signal being proportional to an amount of the marker mimecan present in the sample of the individual, whereby a concentration of the marker mimecan within the sample of the individual based on the quantified signal calculated;
   comparing the calculated concentration value of the marker mimecan within the sample of the individual determined in said step of quantifying to an established diagnostic reference concentration of the marker mimecan, the reference concentration of the marker mimecan set at 90% specificity; and
   providing a diagnosis of heart failure in the individual if the calculated concentration value of the marker mimecan is greater than the established diagnostic reference concentration of the marker mimecan.

2. The method according to claim 1, wherein said step of contacting comprises an enzyme-linked immunosorbent assay application.

3. The method according to claim 1 further comprising the steps of:
   contacting, in-vitro, a portion of a sample from an individual with an antibody or fragment thereof having specific binding affinity for one of a natriuretic peptide marker, a cardiac troponin marker, and a marker of inflammation;
   calculating a concentration of the one of the natriuretic peptide marker, the cardiac troponin marker, and the marker of inflammation within the sample based on said step of contacting; and
   comparing the concentration of the one of the natriuretic peptide marker, the cardiac troponin marker, and the marker of inflammation determined in said step of calculating to a reference concentration of the one of the natriuretic peptide marker, the cardiac troponin marker, and the marker of inflammation, respectively,
   wherein said step of providing comprises providing a diagnosis of heart failure if the concentration of the marker mimecan determined in said step of calculating is greater than the reference concentration of the marker mimecan and the concentration of the one of the natriuretic peptide marker, the cardiac troponin marker, and the marker of inflammation determined in said calculating is greater than the reference concentration for the one of the natriuretic peptide marker, the cardiac troponin marker, and the marker of inflammation determined in said calculating, respectively.

4. The method of claim 3, wherein the reference concentration of the marker mimecan and the one of the natriuretic peptide marker, the cardiac troponin marker, and the marker of inflammation are established in a same control sample.

5. The method according to claim 3, further characterized in that the at least one additional marker is NT-proBNP.

6. The method according to claim 3, further characterized in that the at least one additional marker is troponin T.

7. The method of claim 1, wherein the reference concentration of the marker mimecan is established in a control sample.

8. The method of claim 7, further comprising the steps of:
   contacting, in-vitro, a portion of the control sample with the antibody or fragment thereof having specific binding affinity for the marker mimecan; and
   calculating the reference concentration of the marker mimecan within the control sample based on said step of contacting.

9. The method according to claim 8, wherein the control sample comprises a body fluid.

10. The method according to claim 9, wherein the body fluid is selected from the group consisting of plasma, whole blood, and serum.

11. The method according to claim 8, wherein said step of calculating the reference concentration is performed concurrently with said step of calculating the concentration of the marker mimecan.

12. The method of claim 1, wherein said step of quantifying the signal comprises use of a computing device.

13. The method of claim 1, wherein said step of providing a diagnosis comprises use of a computing device.

14. The method of claim 1, wherein said step of providing a diagnosis comprises providing a diagnosis of heart failure in the individual only if the concentration of the marker mimecan determined in said step of quantifying is 1.5 times greater than the reference concentration of the marker mimecan.

* * * * *

SEQUENCE LISTING

```
<160> NUMBER OF SEQ ID NOS: 1

<210> SEQ ID NO 1
<211> LENGTH: 298
<212> TYPE: PRT
<213> ORGANISM: Homo sapiens

<400> SEQUENCE: 1

Met Lys Thr Leu Gln Ser Thr Leu Leu Leu Leu Leu Val Pro Leu
1               5                   10                  15

Ile Lys Pro Ala Pro Pro Thr Gln Gln Asp Ser Arg Ile Ile Tyr Asp
            20                  25                  30

Tyr Gly Thr Asp Asn Phe Glu Glu Ser Ile Phe Ser Gln Asp Tyr Glu
        35                  40                  45

Asp Lys Tyr Leu Asp Gly Lys Asn Ile Lys Glu Lys Glu Thr Val Ile
    50                  55                  60

Ile Pro Asn Glu Lys Ser Leu Gln Leu Gln Lys Asp Glu Ala Ile Thr
65                  70                  75                  80

Pro Leu Pro Pro Lys Lys Glu Asn Asp Glu Met Pro Thr Cys Leu Leu
                85                  90                  95

Cys Val Cys Leu Ser Gly Ser Val Tyr Cys Glu Glu Val Asp Ile Asp
            100                 105                 110

Ala Val Pro Pro Leu Pro Lys Glu Ser Ala Tyr Leu Tyr Ala Arg Phe
        115                 120                 125

Asn Lys Ile Lys Lys Leu Thr Ala Lys Asp Phe Ala Asp Ile Pro Asn
    130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
            180                 185                 190

Asn Ala Lys Tyr Asn Lys Ile Lys Ser Arg Gly Ile Lys Ala Asn Ala
        195                 200                 205

Phe Lys Lys Leu Asn Asn Leu Thr Phe Leu Tyr Leu Asp His Asn Ala
    210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
            260                 265                 270

Glu Gly Asn Pro Ile Val Leu Gly Lys His Pro Asn Ser Phe Ile Cys
        275                 280                 285
```

```
Leu Lys Arg Leu Pro Ile Gly Ser Tyr Phe
290                 295
```